US012365917B2

(12) United States Patent
Schaefer et al.

(10) Patent No.: US 12,365,917 B2
(45) Date of Patent: Jul. 22, 2025

(54) IMMORTALIZATION OF SPLENIC AND PERIPHERAL BLOOD MACROPHAGES USING A MULTI-CISTRONIC V-RAF/V-MYC LENTIVIRUS

(71) Applicant: The Henry M. Jackson Foundation for the Advancement of Military Medicine, Inc., Bethesda, MD (US)

(72) Inventors: Brian C. Schaefer, Columbia, MD (US); Chelsi Beauregard, Rockville, MD (US)

(73) Assignee: THE HENRY M. JACKSON FOUNDATION FOR THE ADVANCEMENT OF MILITARY MEDICINE, INC., Bethesda, MD (US)

( * ) Notice: Subject to any disclaimer, the term of this patent is extended or adjusted under 35 U.S.C. 154(b) by 1275 days.

(21) Appl. No.: 16/982,977

(22) PCT Filed: Mar. 19, 2019

(86) PCT No.: PCT/US2019/023010
§ 371 (c)(1),
(2) Date: Sep. 21, 2020

(87) PCT Pub. No.: WO2019/183124
PCT Pub. Date: Sep. 26, 2019

(65) Prior Publication Data
US 2021/0017540 A1 Jan. 21, 2021

Related U.S. Application Data

(60) Provisional application No. 62/645,092, filed on Mar. 19, 2018.

(51) Int. Cl.
| | |
|---|---|
| *C12N 15/113* | (2010.01) |
| *C12N 5/0786* | (2010.01) |
| *C12N 9/22* | (2006.01) |
| *C12N 15/11* | (2006.01) |
| *C12N 15/86* | (2006.01) |
| *G01N 33/569* | (2006.01) |

(52) U.S. Cl.
CPC ........... *C12N 15/86* (2013.01); *C12N 5/0645* (2013.01); *G01N 33/56966* (2013.01); *C12N 2506/115* (2013.01); *C12N 2533/70* (2013.01); *C12N 2740/15043* (2013.01); *C12N 2810/6081* (2013.01); *G01N 2333/70596* (2013.01)

(58) Field of Classification Search
CPC .............................. C12N 15/86; C12N 5/0645; C12N 2506/115; C12N 2533/70; C12N 2740/15043; C12N 2810/6081; C12N 2740/16043; G01N 33/56966
See application file for complete search history.

(56) References Cited

U.S. PATENT DOCUMENTS

| | | | | |
|---|---|---|---|---|
| 5,256,553 | A | * 10/1993 | Overell | C12N 15/86 435/456 |
| 2013/0316366 | A1 | * 11/2013 | Yu | C12N 15/86 435/320.1 |

OTHER PUBLICATIONS

Mitchell, T., Hildeman, D., Kedl, R. et al. Immunological adjuvants promote activated T cell survival via induction of Bcl-3. Nat Immunol 2, 397-402 (2001). (Year: 2001).*
S. M. Mansour Haeryfar, David W. Hoskin; Thy-1: More than a Mouse Pan-T Cell Marker1. J Immunol Sep. 15, 2004; 173 (6):3581-3588. (Year: 2004).*
Merten OW, Hebben M, Bovolenta C. Production of lentiviral vectors. Mol Ther Methods Clin Dev. Apr. 13, 2016;3:16017. doi: 10.1038/mtm.2016.17. PMID: 27110581; PMCID: PMC4830361. (Year: 2016).*
UniProtKB Accession No. P01831 (Year: 1988).*
UniProtKB Accession No. P05625 (Year: 1988).*
International Search Report issued in corresponding International Patent Application No. PCT/US2019/023010 dated Jun. 17, 2019.
Written Opinion issued in corresponding International Patent Application No. PCT/US2019/023010 dated Jun. 17, 2019.
UniProtKB Accession No. P0C0N8 (MYC_AVIME) "Viral myc transforming protein," Avia retrovirus MH2E21, Nov. 22, 2005, <<https//www.uniprot.org/uniprot/P0C0N8>>.
Beauregard, et al, "Immortalization of splenic and peripheral blood macrophages using a multi-cistronic v-Raf/v-Myc lentivirus", May 2018. Journal of Immunology, 200 (1 Supplement) Abstract only.
Blasi, et al, "Selective Immortalization of murine macrophages from fresh bone marrow by a RAF/MYC recombinant murine retrovirus", Dec. 1985. Nature Publishing Group, vol. 318, No. 6047, pp. 667-670.
Office Action for European Application No. 19770613.8, Dated Aug. 20, 2024, 6 pages.

* cited by examiner

*Primary Examiner* — Richard A Schnizer
*Assistant Examiner* — Amanda M Zahorik
(74) *Attorney, Agent, or Firm* — Lee & Hayes, P.C.

(57) ABSTRACT

Vectors and methods are disclosed for immortalizing mammalian cells by co-expression of v-raf and v-myc proteins. A replication-defective viral vector is used for improved safety. The vector comprises an optional marker gene, and is especially useful for producing an immortalized macrophage by a method that involves contacting the vector with a monocyte, proliferatively growing the monocyte, growing the monocytic cell on a solid surface, and then growing the monocytic cell on a porous surface. An immortalized macrophage is also disclosed.

9 Claims, 17 Drawing Sheets
Specification includes a Sequence Listing.

FIG. 1A

| Position | Description | Length |
|---|---|---|
| Met-1 | Removed by host | |
| 2-538 | Gag polyprotein | 537 |
| 2-131 | Matrix protein p15 | 130 |
| 132-215 | RNA-binding phosphoprotein p12 | 84 |
| 216-478 | Capsid protein p30 | 263 |
| 479-538 | Nucleocapsid protein p10 | 60 |

FIG. 1B

```
            10         20         30         40         50
     MGQTVTTPLS LTLGHWKDVE RIAHNQSVDV KKRRWVTFCS AEWPTFNVGW
            60         70         80         90        100
     PRDGTFNRDL ITQVKIKVFS PGPHGHPDQV PYIVTWEALA FDPPPWVKPF
           110        120        130        140        150
     VHPKPPPPLP PSAPSLPLEP PRSTPPRSSL YPALTPSLGA KPKPQVLSDS
           160        170        180        190        200
     GGPLIDLLTE DPPPYRDPRP PPSDRDGNGG EATPAGEAPD PSPMASRLRG
           210        220        230        240        250
     RREPPVADST TSQAFPLRAG GNGQLQYWPF SSSDLYNWKN NNPSFSEDPG
           260        270        280        290        300
     KLTALIESVL ITHQPTWDDC QQLLGTLLTG EEKQRVLLEA RKAVRGDDGR
           310        320        330        340        350
     PTQLPNEVDA AFPLERPDWD YTTQAGRNHL VHYRQLLLAG LQNAGRSPTN
           360        370        380        390        400
     LAKVKGITQG PNESPSAFLE RLKEAYRRYT PYDPEDPGQE TNVSMSFIWQ
           410        420        430        440        450
     SAPDIGRKLE RLEDLKNKTL GDLVREAEKI FNKRETPEER EERIRRETEE
           460        470        480        490        500
     KEERRRTEDE QKEKERDRRR HREMSKLLAT VVSGQKQDRQ GGERRRSQLD
           510        520        530
     RDQCAYCKEK GHWAKDCPKK PRGPRGPRPQ TSLLTLDD
```

FIG. 2

C-terminus of Gag region

```
N  E  S  P  S  A  F  L  E  R  L  K  E  A  Y  R  R  Y  T  P
N  E  S  P  S  A  F  L  E  R  L  K  E  A  Y  R  R  Y  T  P
ATGAGTCTCCCTCGGCCTTCCTAGAGAGACTTAAGGAAGCCTATCGCAGGTACACTCC
        2,890      2,900      2,910      2,920      2,930      2,940
```

N-terminus of v-Raf portion

```
Y  D  P  G  T
Y  D  P  G  T  Q  E  K  N  K  I  R  P  R  G  Q  R  D
TTATGACCCTGGGACCCAGGAAAAAAACAAAATTAGGCCTCGTGGGCAGAGAGAC
        2,950      2,960      2,970      2,980      2,990
```

FIG. 3

```
                                      Linker
  v-Raf (Cterminus)       K  L  L  Y  K  A  G  G  R  V
  T  R  L  P  V  F                                       E  G  R  G  S
CACAAGACTGCCTGTTTTTAAGCTTCTGTACAAGGCCGGCGGACGCGTGGAGGGCAGAGGAAGT
  |         |         |         |         |         |         |
3,910     3,920     3,930     3,940     3,950     3,960     3,970 v-Myc (N-terminus)
                                                    Linker
                                                    G   S
      T2A
  L  L  T  C  G  D  V  E  E  N  P  G  P             M  P  L  S
CTTCTAACATGTGGTGACGTCGAGGAGAATCCCGGCCCTGGATCCATGCCGCTCAGC
   |         |         |         |         |         |
 3,980     3,990     4,000     4,010     4,020
```

LIVeMac

FIG. 5

Thy1.1 C-terminus
```
                          Linker
                        A  S  E  F  G                                    P2A
 Q  A  L  D  F  I  S  L                    A  T  N  F  S  L  L  K  Q   A
CAAGCCCTGGACTTCATTTCTCTGGCATCCGAATTCGGAGCCACCAACTTTTCTCTGCTCAAGCAGGC
     2,910      2,920      2,930      2,940      2,950      2,960      2,970
```

```
                      Linker     p30Gag-vRaf N-terminus
                     A  S
                 Cleavage site         P  L  R  T  G  G  N  G  Q  L
 G  D  V  E  E  N  P  G  P             P  L  R  T  G  G  N  G  Q  L
TGGAGATGTGGAAGAAAACCCAGGACCTGCTAGCCCCCTCCGCACAGGAGGAAACGGACAGCT
     2,980      2,990      3,000      3,010      3,020      3,030
```

LIVeMac-Thy1.1-v1

LIVeMac-Thy1.1-v2

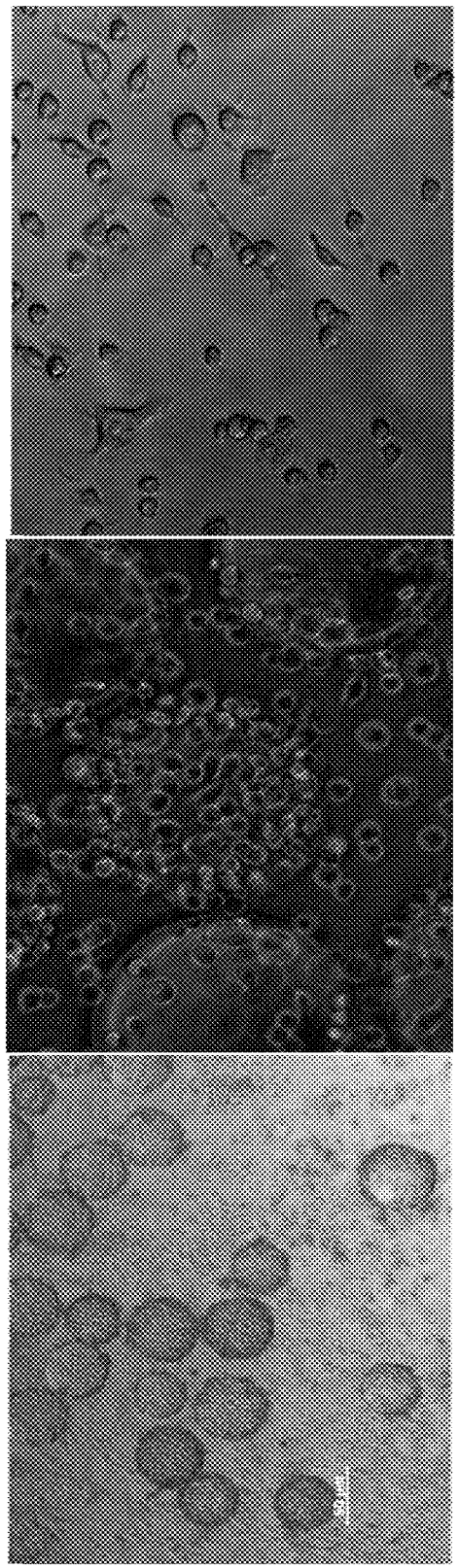

SEQUENCE LISTING

```
<160> NUMBER OF SEQ ID NOS: 13

<210> SEQ ID NO 1
<211> LENGTH: 937
<212> TYPE: PRT
<213> ORGANISM: Artificial Sequence
<220> FEATURE:
<223> OTHER INFORMATION: Synthetic Sequence (p30Gag-vRaf-T2A-vMyc fusion
      protein of LIVeMac)

<400> SEQUENCE: 1

Met Pro Leu Arg Thr Gly Gly Asn Gly Gln Leu Gln Tyr Trp Pro Phe
1               5                   10                  15

Ser Ser Ser Asp Leu Tyr Asn Trp Arg Asn Asn Asn Pro Ser Phe Ser
                20                  25                  30

Glu Asp Pro Gly Lys Leu Thr Ala Leu Ile Glu Ser Val Leu Ile Thr
            35                  40                  45

His Gln Pro Thr Trp Asp Asp Cys Gln Gln Leu Leu Gly Thr Leu Leu
        50                  55                  60

Thr Gly Glu Glu Lys Gln Arg Val Leu Leu Glu Ala Arg Lys Ala Val
65                  70                  75                  80

Arg Gly Asp Asp Gly Arg Pro Thr Gln Leu Pro Asn Glu Val Asp Ala
                85                  90                  95

Ala Phe Pro Leu Glu Arg Pro Asp Trp Glu Tyr Thr Thr Gln Arg Gly
            100                 105                 110

Arg Asn His Leu Val Leu Tyr Arg Gln Leu Leu Leu Ala Gly Leu Gln
        115                 120                 125

Asn Ala Gly Arg Ser Pro Thr Asn Leu Ala Lys Val Lys Gly Ile Thr
    130                 135                 140

Gln Gly Pro Asn Glu Ser Pro Ser Ala Phe Leu Glu Arg Leu Lys Glu
145                 150                 155                 160

Ala Tyr Arg Arg Tyr Thr Pro Tyr Asp Pro Gly Thr Gln Glu Lys Asn
                165                 170                 175
```

-continued

```
Lys Ile Arg Pro Arg Gly Gln Arg Asp Ser Ser Tyr Tyr Trp Lys Ile
            180                 185                 190
Glu Ala Ser Glu Val Met Leu Ser Thr Arg Ile Gly Ser Gly Ser Phe
            195                 200                 205
Gly Thr Val Tyr Lys Gly Lys Trp His Gly Asp Val Ala Val Lys Ile
210                 215                 220
Leu Lys Val Val Asp Pro Thr Pro Glu Gln Leu Gln Ala Phe Arg Asn
225                 230                 235                 240
Glu Val Ala Val Leu Arg Lys Thr Arg His Val Asn Ile Leu Leu Phe
                245                 250                 255
Met Gly Tyr Met Thr Lys Asp Asn Leu Ala Ile Val Thr Gln Trp Cys
                260                 265                 270
Glu Gly Ser Ser Leu Tyr Lys His Leu His Val Gln Glu Thr Lys Phe
            275                 280                 285
Gln Met Phe Gln Leu Ile Asp Ile Ala Arg Gln Thr Ala Gln Gly Met
            290                 295                 300
Asp Tyr Leu His Ala Lys Asn Ile Ile His Arg Asp Met Lys Ser Asn
305                 310                 315                 320
Asn Ile Phe Leu His Glu Gly Leu Thr Val Lys Ile Gly Asp Phe Gly
                325                 330                 335
Leu Ala Thr Val Lys Ser Arg Trp Ser Gly Ser Gln Gln Val Glu Gln
                340                 345                 350
Pro Thr Gly Ser Ile Leu Trp Met Ala Pro Glu Val Ile Arg Met Gln
            355                 360                 365
Asp Ser Asn Pro Phe Ser Phe Gln Ser Asp Val Tyr Ser Tyr Gly Ile
            370                 375                 380
Val Leu Tyr Glu Leu Met Thr Gly Glu Leu Pro Tyr Ser His Ile Asn
385                 390                 395                 400
Asn Arg Asp Gln Ile Ile Phe Met Val Gly Arg Gly Tyr Ala Ser Pro
                405                 410                 415
Asp Leu Ser Lys Leu Tyr Lys Asn Cys Pro Lys Ala Met Lys Arg Leu
                420                 425                 430
Val Ala Asp Cys Leu Lys Lys Val Arg Glu Glu Arg Pro Leu Phe Pro
            435                 440                 445
Gln Ile Leu Ser Ser Ile Ala Leu Leu Gln His Ser Leu Pro Lys Ile
            450                 455                 460
Asn Arg Ser Ala Ser Glu Pro Ser Leu His Arg Ala Ser His Thr Glu
465                 470                 475                 480
Asp Ile Asn Ser Cys Thr Leu Thr Ser Thr Arg Leu Pro Val Phe Lys
                485                 490                 495
Leu Leu Tyr Lys Ala Gly Gly Arg Val Glu Gly Arg Gly Ser Leu Leu
                500                 505                 510
Thr Cys Gly Asp Val Glu Glu Asn Pro Gly Pro Gly Ser Met Pro Leu
            515                 520                 525
Ser Val Ser Leu Pro Ser Lys Asn Tyr Asp Tyr Asp Tyr Asp Ser Val
            530                 535                 540
Gln Pro Tyr Phe Tyr Phe Glu Glu Glu Glu Asn Phe Tyr Leu Ala
545                 550                 555                 560
Ala Gln Gln Arg Ser Ser Glu Leu Gln Pro Pro Ala Pro Ser Glu Asp
                565                 570                 575
Ile Trp Lys Lys Phe Glu Leu Leu Pro Ala Pro Pro Leu Ser Pro Ser
                580                 585                 590
Cys Arg Ser Asn Leu Ala Ala Ala Ser Cys Phe Pro Ser Thr Ala Asp
```

```
                    595                 600                 605
Gln Leu Glu Met Val Thr Glu Leu Leu Gly Gly Asp Met Val Asn Gln
    610                 615                 620

Ser Ser Ile Cys Asp Pro Asp Glu Ser Phe Val Lys Ser Ile Ile
625                 630                 635                 640

Ile Arg Asp Cys Met Trp Ser Gly Phe Ser Ala Ala Lys Leu Glu
                645                 650                 655

Lys Val Val Ser Glu Lys Leu Ala Thr Tyr Lys Ala Ser Arg Arg Glu
                660                 665                 670

Gly Gly Pro Ala Ala Ser Arg Pro Gly Pro Pro Ser Gly Pro
            675                 680                 685

Pro Pro Pro Ala Gly Pro Ala Ala Ser Ala Gly Leu Tyr Leu His
690                 695                 700

Asp Leu Gly Ala Ala Ala Gly Cys Ile Gly Ser Ser Val Val Phe
705                 710                 715                 720

Pro Cys Pro Leu Gly Arg Arg Gly Pro Pro Gly Ala Gly Pro Ala Ala
                725                 730                 735

Leu Leu Gly Val Asp Ala Pro Thr Ala Gly Gly Ser Glu Glu
            740                 745                 750

Glu Gln Glu Glu Asp Glu Glu Ile Asp Val Val Thr Leu Ala Glu Ala
                755                 760                 765

Asn Glu Ser Glu Ser Ser Thr Glu Ser Thr Glu Ala Ser Glu Glu
770                 775                 780

His Cys Lys Pro His His Ser Pro Leu Val Leu Lys Arg Cys His Val
785                 790                 795                 800

Asn Ile His Gln His Asn Tyr Ala Ala Pro Ser Thr Lys Val Glu
                805                 810                 815

Tyr Pro Ala Ala Lys Arg Leu Lys Leu Asp Ser Gly Arg Val Leu Lys
                820                 825                 830

Gln Ile Ser Asn Asn Arg Lys Cys Ser Ser Pro Arg Thr Leu Asp Ser
                835                 840                 845

Glu Glu Asn Asp Lys Arg Arg Thr His Asn Val Leu Glu Arg Gln Arg
                850                 855                 860

Arg Asn Glu Leu Lys Leu Arg Phe Phe Ala Leu Arg Asp Gln Ile Pro
865                 870                 875                 880

Glu Val Ala Asn Asn Glu Lys Ala Pro Lys Val Val Ile Leu Lys Lys
                885                 890                 895

Ala Thr Glu Tyr Val Leu Ser Leu Gln Ser Asp Glu His Lys Leu Ile
                900                 905                 910

Ala Glu Lys Glu Gln Leu Arg Arg Arg Glu Gln Leu Lys His Asn
            915                 920                 925

Leu Glu Gln Leu Arg Asn Ser Arg Ala
    930                 935

<210> SEQ ID NO 2
<211> LENGTH: 1124
<212> TYPE: PRT
<213> ORGANISM: Artificial Sequence
<220> FEATURE:
<223> OTHER INFORMATION: Synthetic Sequence (Thy1.1-P2A- p30Gag-vRaf-
      T2A-vMyc fusion protein of LIVeMac-Thy1.1-v1 )

<400> SEQUENCE: 2

Met Asn Pro Ala Ile Ser Val Ala Leu Leu Leu Ser Val Leu Gln Val
1               5                   10                  15
```

-continued

Ser Arg Gly Gln Lys Val Thr Ser Leu Thr Ala Cys Leu Val Asn Gln
            20                  25                  30

Asn Leu Arg Leu Asp Cys Arg His Glu Asn Asn Thr Lys Asp Asn Ser
        35                  40                  45

Ile Gln His Glu Phe Ser Leu Thr Arg Glu Lys Arg Lys His Val Leu
    50                  55                  60

Ser Gly Thr Leu Gly Ile Pro Glu His Thr Tyr Arg Ser Arg Val Thr
65                  70                  75                  80

Leu Ser Asn Gln Pro Tyr Ile Lys Val Leu Thr Leu Ala Asn Phe Thr
                85                  90                  95

Thr Lys Asp Glu Gly Asp Tyr Phe Cys Glu Leu Arg Val Ser Gly Ala
            100                 105                 110

Asn Pro Met Ser Ser Asn Lys Ser Ile Ser Val Tyr Arg Asp Lys Leu
        115                 120                 125

Val Lys Cys Gly Gly Ile Ser Leu Leu Val Gln Asn Thr Ser Trp Met
    130                 135                 140

Leu Leu Leu Leu Leu Ser Leu Ser Leu Leu Gln Ala Leu Asp Phe Ile
145                 150                 155                 160

Ser Leu Ala Ser Glu Phe Gly Ala Thr Asn Phe Ser Leu Leu Lys Gln
                165                 170                 175

Ala Gly Asp Val Glu Glu Asn Pro Gly Pro Ala Ser Pro Leu Arg Thr
            180                 185                 190

Gly Gly Asn Gly Gln Leu Gln Tyr Trp Pro Phe Ser Ser Ser Asp Leu
        195                 200                 205

Tyr Asn Trp Arg Asn Asn Asn Pro Ser Phe Ser Glu Asp Pro Gly Lys
    210                 215                 220

Leu Thr Ala Leu Ile Glu Ser Val Leu Ile Thr His Gln Pro Thr Trp
225                 230                 235                 240

Asp Asp Cys Gln Gln Leu Leu Gly Thr Leu Leu Thr Gly Glu Glu Lys
                245                 250                 255

Gln Arg Val Leu Leu Glu Ala Arg Lys Ala Val Arg Gly Asp Asp Gly
            260                 265                 270

Arg Pro Thr Gln Leu Pro Asn Glu Val Asp Ala Ala Phe Pro Leu Glu
        275                 280                 285

Arg Pro Asp Trp Glu Tyr Thr Thr Gln Arg Gly Arg Asn His Leu Val
    290                 295                 300

Leu Tyr Arg Gln Leu Leu Leu Ala Gly Leu Gln Asn Ala Gly Arg Ser
305                 310                 315                 320

Pro Thr Asn Leu Ala Lys Val Lys Gly Ile Thr Gln Gly Pro Asn Glu
                325                 330                 335

Ser Pro Ser Ala Phe Leu Glu Arg Leu Lys Glu Ala Tyr Arg Arg Tyr
            340                 345                 350

Thr Pro Tyr Asp Pro Gly Thr Gln Glu Lys Asn Lys Ile Arg Pro Arg
        355                 360                 365

Gly Gln Arg Asp Ser Ser Tyr Tyr Trp Lys Ile Glu Ala Ser Glu Val
    370                 375                 380

Met Leu Ser Thr Arg Ile Gly Ser Gly Ser Phe Gly Thr Val Tyr Lys
385                 390                 395                 400

Gly Lys Trp His Gly Asp Val Ala Val Lys Ile Leu Lys Val Val Asp
                405                 410                 415

Pro Thr Pro Glu Gln Leu Gln Ala Phe Arg Asn Glu Val Ala Val Leu
            420                 425                 430

Arg Lys Thr Arg His Val Asn Ile Leu Leu Phe Met Gly Tyr Met Thr

```
                435                 440                 445
Lys Asp Asn Leu Ala Ile Val Thr Gln Trp Cys Glu Gly Ser Ser Leu
450                 455                 460

Tyr Lys His Leu His Val Gln Glu Thr Lys Phe Gln Met Phe Gln Leu
465                 470                 475                 480

Ile Asp Ile Ala Arg Gln Thr Ala Gln Gly Met Asp Tyr Leu His Ala
                485                 490                 495

Lys Asn Ile Ile His Arg Asp Met Lys Ser Asn Asn Ile Phe Leu His
                500                 505                 510

Glu Gly Leu Thr Val Lys Ile Gly Asp Phe Gly Leu Ala Thr Val Lys
            515                 520                 525

Ser Arg Trp Ser Gly Ser Gln Gln Val Glu Gln Pro Thr Gly Ser Ile
530                 535                 540

Leu Trp Met Ala Pro Glu Val Ile Arg Met Gln Asp Ser Asn Pro Phe
545                 550                 555                 560

Ser Phe Gln Ser Asp Val Tyr Ser Tyr Gly Ile Val Leu Tyr Glu Leu
                565                 570                 575

Met Thr Gly Glu Leu Pro Tyr Ser His Ile Asn Asn Arg Asp Gln Ile
            580                 585                 590

Ile Phe Met Val Gly Arg Gly Tyr Ala Ser Pro Asp Leu Ser Lys Leu
        595                 600                 605

Tyr Lys Asn Cys Pro Lys Ala Met Lys Arg Leu Val Ala Asp Cys Leu
610                 615                 620

Lys Lys Val Arg Glu Glu Arg Pro Leu Phe Pro Gln Ile Leu Ser Ser
625                 630                 635                 640

Ile Ala Leu Leu Gln His Ser Leu Pro Lys Ile Asn Arg Ser Ala Ser
                645                 650                 655

Glu Pro Ser Leu His Arg Ala Ser His Thr Glu Asp Ile Asn Ser Cys
                660                 665                 670

Thr Leu Thr Ser Thr Arg Leu Pro Val Phe Lys Leu Leu Tyr Lys Ala
            675                 680                 685

Gly Gly Arg Val Glu Gly Arg Gly Ser Leu Leu Thr Cys Gly Asp Val
        690                 695                 700

Glu Glu Asn Pro Gly Pro Gly Ser Met Pro Leu Ser Val Ser Leu Pro
705                 710                 715                 720

Ser Lys Asn Tyr Asp Tyr Asp Tyr Asp Ser Val Gln Pro Tyr Phe Tyr
                725                 730                 735

Phe Glu Glu Glu Glu Glu Asn Phe Tyr Leu Ala Ala Gln Gln Arg Ser
                740                 745                 750

Ser Glu Leu Gln Pro Pro Ala Pro Ser Glu Asp Ile Trp Lys Lys Phe
            755                 760                 765

Glu Leu Leu Pro Ala Pro Pro Leu Ser Pro Ser Cys Arg Ser Asn Leu
        770                 775                 780

Ala Ala Ala Ser Cys Phe Pro Ser Thr Ala Asp Gln Leu Glu Met Val
785                 790                 795                 800

Thr Glu Leu Leu Gly Gly Asp Met Val Asn Gln Ser Ser Ile Cys Asp
                805                 810                 815

Pro Asp Asp Glu Ser Phe Val Lys Ser Ile Ile Arg Asp Cys Met
                820                 825                 830

Trp Ser Gly Phe Ser Ala Ala Lys Leu Glu Lys Val Val Ser Glu
            835                 840                 845

Lys Leu Ala Thr Tyr Lys Ala Ser Arg Arg Glu Gly Gly Pro Ala Ala
850                 855                 860
```

```
Ala Ser Arg Pro Gly Pro Pro Ser Gly Pro Pro Pro Ala
865                 870                 875                 880

Gly Pro Ala Ala Ser Ala Gly Leu Tyr Leu His Asp Leu Gly Ala Ala
                885                 890                 895

Ala Ala Gly Cys Ile Gly Ser Ser Val Val Phe Pro Cys Pro Leu Gly
            900                 905                 910

Arg Arg Gly Pro Pro Gly Ala Gly Pro Ala Ala Leu Leu Gly Val Asp
            915                 920                 925

Ala Pro Pro Thr Ala Gly Gly Ser Glu Glu Gln Glu Glu Asp
930                 935                 940

Glu Glu Ile Asp Val Val Thr Leu Ala Glu Ala Asn Glu Ser Glu Ser
945                 950                 955                 960

Ser Thr Glu Ser Thr Glu Ala Ser Glu Glu His Cys Lys Pro His
                965                 970                 975

His Ser Pro Leu Val Leu Lys Arg Cys His Val Asn Ile His Gln His
            980                 985                 990

Asn Tyr Ala Ala Pro Pro Ser Thr  Lys Val Glu Tyr Pro  Ala Ala Lys
            995                 1000                1005

Arg Leu  Lys Leu Asp Ser Gly  Arg Val Leu Lys Gln  Ile Ser Asn
    1010                1015                1020

Asn Arg  Lys Cys Ser Ser Pro  Arg Thr Leu Asp Ser  Glu Glu Asn
    1025                1030                1035

Asp Lys  Arg Arg Thr His Asn  Val Leu Glu Arg Gln  Arg Arg Asn
    1040                1045                1050

Glu Leu  Lys Leu Arg Phe Phe  Ala Leu Arg Asp Gln  Ile Pro Glu
    1055                1060                1065

Val Ala  Asn Asn Glu Lys Ala  Pro Lys Val Val Ile  Leu Lys Lys
    1070                1075                1080

Ala Thr  Glu Tyr Val Leu Ser  Leu Gln Ser Asp Glu  His Lys Leu
    1085                1090                1095

Ile Ala  Glu Lys Glu Gln Leu  Arg Arg Arg Arg Glu  Gln Leu Lys
    1100                1105                1110

His Asn  Leu Glu Gln Leu Arg  Asn Ser Arg Ala
    1115                1120

<210> SEQ ID NO 3
<211> LENGTH: 162
<212> TYPE: PRT
<213> ORGANISM: Mus musculus

<400> SEQUENCE: 3

Met Asn Pro Ala Ile Ser Val Ala Leu Leu Leu Ser Val Leu Gln Val
1               5                   10                  15

Ser Arg Gly Gln Lys Val Thr Ser Leu Thr Ala Cys Leu Val Asn Gln
                20                  25                  30

Asn Leu Arg Leu Asp Cys Arg His Glu Asn Asn Thr Lys Asp Asn Ser
            35                  40                  45

Ile Gln His Glu Phe Ser Leu Thr Arg Glu Lys Arg Lys His Val Leu
        50                  55                  60

Ser Gly Thr Leu Gly Ile Pro Glu His Thr Tyr Arg Ser Arg Val Thr
65                  70                  75                  80

Leu Ser Asn Gln Pro Tyr Ile Lys Val Leu Thr Leu Ala Asn Phe Thr
                85                  90                  95

Thr Lys Asp Glu Gly Asp Tyr Phe Cys Glu Leu Arg Val Ser Gly Ala
```

```
              100                 105                 110
Asn Pro Met Ser Ser Asn Lys Ser Ile Ser Val Tyr Arg Asp Lys Leu
            115                 120                 125

Val Lys Cys Gly Gly Ile Ser Leu Leu Val Gln Asn Thr Ser Trp Met
130                 135                 140

Leu Leu Leu Leu Leu Ser Leu Ser Leu Leu Gln Ala Leu Asp Phe Ile
145                 150                 155                 160

Ser Leu

<210> SEQ ID NO 4
<211> LENGTH: 323
<212> TYPE: PRT
<213> ORGANISM: Moloney murine leukemia virus

<400> SEQUENCE: 4

Gln Glu Lys Asn Lys Ile Arg Pro Arg Gly Gln Arg Asp Ser Ser Tyr
1               5                   10                  15

Tyr Trp Lys Ile Glu Ala Ser Glu Val Met Leu Ser Thr Arg Ile Gly
            20                  25                  30

Ser Gly Ser Phe Gly Thr Val Tyr Lys Gly Lys Trp His Gly Asp Val
        35                  40                  45

Ala Val Lys Ile Leu Lys Val Val Asp Pro Thr Pro Glu Gln Leu Gln
50                  55                  60

Ala Phe Arg Asn Glu Val Ala Val Leu Arg Lys Thr Arg His Val Asn
65                  70                  75                  80

Ile Leu Leu Phe Met Gly Tyr Met Thr Lys Asp Asn Leu Ala Ile Val
                85                  90                  95

Thr Gln Trp Cys Glu Gly Ser Ser Leu Tyr Lys His Leu His Val Gln
            100                 105                 110

Glu Thr Lys Phe Gln Met Phe Gln Leu Ile Asp Ile Ala Arg Gln Thr
        115                 120                 125

Ala Gln Gly Met Asp Tyr Leu His Ala Lys Asn Ile Ile His Arg Asp
    130                 135                 140

Met Lys Ser Asn Asn Ile Phe Leu His Glu Gly Leu Thr Val Lys Ile
145                 150                 155                 160

Gly Asp Phe Gly Leu Ala Thr Val Lys Ser Arg Trp Ser Gly Ser Gln
                165                 170                 175

Gln Val Glu Gln Pro Thr Gly Ser Ile Leu Trp Met Ala Pro Glu Val
            180                 185                 190

Ile Arg Met Gln Asp Ser Asn Pro Phe Ser Phe Gln Ser Asp Val Tyr
        195                 200                 205

Ser Tyr Gly Ile Val Leu Tyr Glu Leu Met Thr Gly Glu Leu Pro Tyr
    210                 215                 220

Ser His Ile Asn Asn Arg Asp Gln Ile Ile Phe Met Val Gly Arg Gly
225                 230                 235                 240

Tyr Ala Ser Pro Asp Leu Ser Lys Leu Tyr Lys Asn Cys Pro Lys Ala
                245                 250                 255

Met Lys Arg Leu Val Ala Asp Cys Leu Lys Lys Val Arg Glu Glu Arg
            260                 265                 270

Pro Leu Phe Pro Gln Ile Leu Ser Ser Ile Ala Leu Leu Gln His Ser
        275                 280                 285

Leu Pro Lys Ile Asn Arg Ser Ala Ser Glu Pro Ser Leu His Arg Ala
    290                 295                 300

Ser His Thr Glu Asp Ile Asn Ser Cys Thr Leu Thr Ser Thr Arg Leu
```

-continued

```
              305                 310                 315                 320

Pro Val Phe

<210> SEQ ID NO 5
<211> LENGTH: 412
<212> TYPE: PRT
<213> ORGANISM: Avian carcinoma virus

<400> SEQUENCE: 5

Met Pro Leu Ser Val Ser Leu Pro Ser Lys Asn Tyr Asp Tyr Asp Tyr
1               5                   10                  15

Asp Ser Val Gln Pro Tyr Phe Tyr Phe Glu Glu Glu Glu Asn Phe
                20                  25                  30

Tyr Leu Ala Ala Gln Gln Arg Ser Ser Glu Leu Gln Pro Pro Ala Pro
            35                  40                  45

Ser Glu Asp Ile Trp Lys Lys Phe Glu Leu Leu Pro Ala Pro Pro Leu
    50                  55                  60

Ser Pro Ser Cys Arg Ser Asn Leu Ala Ala Ser Cys Phe Pro Ser
65                  70                  75                  80

Thr Ala Asp Gln Leu Glu Met Val Thr Glu Leu Leu Gly Gly Asp Met
                85                  90                  95

Val Asn Gln Ser Ser Ile Cys Asp Pro Asp Asp Glu Ser Phe Val Lys
                100                 105                 110

Ser Ile Ile Ile Arg Asp Cys Met Trp Ser Gly Phe Ser Ala Ala Ala
            115                 120                 125

Lys Leu Glu Lys Val Val Ser Glu Lys Leu Ala Thr Tyr Lys Ala Ser
130                 135                 140

Arg Arg Glu Gly Gly Pro Ala Ala Ala Ser Arg Pro Gly Pro Pro
145                 150                 155                 160

Ser Gly Pro Pro Pro Pro Ala Gly Pro Ala Ala Ser Ala Gly Leu
                165                 170                 175

Tyr Leu His Asp Leu Gly Ala Ala Ala Gly Cys Ile Gly Ser Ser
            180                 185                 190

Val Val Phe Pro Cys Pro Leu Gly Arg Arg Gly Pro Pro Gly Ala Gly
            195                 200                 205

Pro Ala Ala Leu Leu Gly Val Asp Ala Pro Pro Thr Ala Gly Gly Gly
210                 215                 220

Ser Glu Glu Glu Gln Glu Asp Glu Glu Ile Asp Val Val Thr Leu
225                 230                 235                 240

Ala Glu Ala Asn Glu Ser Glu Ser Ser Thr Glu Ser Ser Thr Glu Ala
                245                 250                 255

Ser Glu Glu His Cys Lys Pro His His Ser Pro Leu Val Leu Lys Arg
            260                 265                 270

Cys His Val Asn Ile His Gln His Asn Tyr Ala Ala Pro Pro Ser Thr
        275                 280                 285

Lys Val Glu Tyr Pro Ala Ala Lys Arg Leu Lys Leu Asp Ser Gly Arg
290                 295                 300

Val Leu Lys Gln Ile Ser Asn Asn Arg Lys Cys Ser Ser Pro Arg Thr
305                 310                 315                 320

Leu Asp Ser Glu Glu Asn Asp Lys Arg Arg Thr His Asn Val Leu Glu
                325                 330                 335

Arg Gln Arg Arg Asn Glu Leu Lys Leu Arg Phe Phe Ala Leu Arg Asp
            340                 345                 350

Gln Ile Pro Glu Val Ala Asn Asn Glu Lys Ala Pro Lys Val Val Ile
```

```
                355                 360                 365
Leu Lys Lys Ala Thr Glu Tyr Val Leu Ser Leu Gln Ser Asp Glu His
        370                 375                 380

Lys Leu Ile Ala Glu Lys Glu Gln Leu Arg Arg Arg Glu Gln Leu
385                 390                 395                 400

Lys His Asn Leu Glu Gln Leu Arg Asn Ser Arg Ala
                405                 410

<210> SEQ ID NO 6
<211> LENGTH: 538
<212> TYPE: PRT
<213> ORGANISM: Artificial Sequence
<220> FEATURE:
<223> OTHER INFORMATION: Synthetic Sequence (cleavage products of the
      Gag polyprotein)

<400> SEQUENCE: 6

Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
            100                 105                 110

Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                245                 250                 255

Glu Ser Val Leu Ile Thr His Gln Pro Thr Trp Asp Asp Cys Gln Gln
            260                 265                 270

Leu Leu Gly Thr Leu Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
    290                 295                 300
```

```
Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
        355                 360                 365

Leu Glu Arg Leu Lys Glu Ala Tyr Arg Arg Tyr Thr Pro Tyr Asp Pro
    370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                405                 410                 415

Asn Lys Thr Leu Gly Asp Leu Val Arg Glu Ala Glu Lys Ile Phe Asn
                420                 425                 430

Lys Arg Glu Thr Pro Glu Glu Arg Glu Arg Ile Arg Arg Glu Thr
            435                 440                 445

Glu Glu Lys Glu Glu Arg Arg Arg Thr Glu Asp Glu Gln Lys Glu Lys
450                 455                 460

Glu Arg Asp Arg Arg Arg His Arg Glu Met Ser Lys Leu Leu Ala Thr
465                 470                 475                 480

Val Val Ser Gly Gln Lys Gln Asp Arg Gln Gly Gly Glu Arg Arg
                485                 490                 495

Ser Gln Leu Asp Arg Asp Gln Cys Ala Tyr Cys Lys Leu Lys Gly His
        500                 505                 510

Trp Ala Lys Asp Cys Pro Lys Lys Pro Arg Gly Pro Arg Gly Pro Arg
        515                 520                 525

Pro Gln Thr Ser Leu Leu Thr Leu Asp Asp
        530                 535

<210> SEQ ID NO 7
<211> LENGTH: 25
<212> TYPE: PRT
<213> ORGANISM: Artificial Sequence
<220> FEATURE:
<223> OTHER INFORMATION: Synthetic Sequence Gag-vRaf junction

<400> SEQUENCE: 7

Asn Glu Ser Pro Ser Ala Phe Leu Glu Arg Leu Lys Glu Ala Tyr Arg
1               5                   10                  15

Arg Tyr Thr Pro Tyr Asp Pro Gly Thr
            20                  25

<210> SEQ ID NO 8
<211> LENGTH: 38
<212> TYPE: PRT
<213> ORGANISM: Artificial Sequence
<220> FEATURE:
<223> OTHER INFORMATION: Synthetic Sequence Gag-vRaf junction

<400> SEQUENCE: 8

Asn Glu Ser Pro Ser Ala Phe Leu Glu Arg Leu Lys Glu Ala Tyr Arg
1               5                   10                  15

Arg Tyr Thr Pro Tyr Asp Pro Gly Thr Gln Glu Lys Asn Lys Ile Arg
            20                  25                  30

Pro Arg Gly Gln Arg Asp
        35
```

<210> SEQ ID NO 9
<211> LENGTH: 113
<212> TYPE: DNA
<213> ORGANISM: Artificial Sequence
<220> FEATURE:
<223> OTHER INFORMATION: Synthetic Sequence Gag-vRaf junction

<400> SEQUENCE: 9

```
atgagtctcc ctcggccttc ctagagagac ttaaggaagc ctatcgcagg tacactcctt    60
atgaccctgg gacccaggaa aaaaacaaaa ttaggcctcg tgggcagaga gac           113
```

<210> SEQ ID NO 10
<211> LENGTH: 40
<212> TYPE: PRT
<213> ORGANISM: Artificial Sequence
<220> FEATURE:
<223> OTHER INFORMATION: Synthetic Sequence vRaf-T2A-vMyc junction

<400> SEQUENCE: 10

Thr Arg Leu Pro Val Phe Lys Leu Leu Tyr Lys Ala Gly Gly Arg Val
1               5                   10                  15

Glu Gly Arg Gly Ser Leu Leu Thr Cys Gly Asp Val Glu Glu Asn Pro
            20                  25                  30

Gly Pro Gly Ser Met Pro Leu Ser
        35                  40

<210> SEQ ID NO 11
<211> LENGTH: 121
<212> TYPE: DNA
<213> ORGANISM: Artificial Sequence
<220> FEATURE:
<223> OTHER INFORMATION: Synthetic Sequence vRaf-T2A-vMyc junction

<400> SEQUENCE: 11

```
cacaagactg cctgtttta agcttctgta caaggccggc ggacgcgtgg agggcagagg     60
aagtcttcta acatgtggtg acgtcgagga gaatcccggc cctggatcca tgccgctcag   120
c                                                                   121
```

<210> SEQ ID NO 12
<211> LENGTH: 44
<212> TYPE: PRT
<213> ORGANISM: Artificial Sequence
<220> FEATURE:
<223> OTHER INFORMATION: Synthetic Sequence Thy1.1-P2A-p30Gag-vRaf
      junction region

<400> SEQUENCE: 12

Gln Ala Leu Asp Phe Ile Ser Leu Ala Ser Glu Phe Gly Ala Thr Asn
1               5                   10                  15

Phe Ser Leu Leu Lys Gln Ala Gly Asp Val Glu Glu Asn Pro Gly Pro
            20                  25                  30

Ala Ser Pro Leu Arg Thr Gly Gly Asn Gly Gln Leu
        35                  40

<210> SEQ ID NO 13
<211> LENGTH: 131
<212> TYPE: DNA
<213> ORGANISM: Artificial Sequence
<220> FEATURE:
<223> OTHER INFORMATION: Synthetic Sequence Thy1.1-P2A-p30Gag-vRaf
      junction region

```
<400> SEQUENCE: 13
caagccctgg acttcatttc tctggcatcc gaattcggag ccaccaactt ttctctgctc      60
aagcaggctg gagatgtgga agaaaaccca ggacctgcta gcccctccg cacaggagga     120 aacggacagc t                                                         131
```

IMMORTALIZATION OF SPLENIC AND PERIPHERAL BLOOD MACROPHAGES USING A MULTI-CISTRONIC V-RAF/V-MYC LENTIVIRUS

STATEMENT REGARDING FEDERALLY SPONSORED RESEARCH OR DEVELOPMENT

This invention was made with government support under Uniformed Services University Program Project Grant MIC-73-2515 (aka HT9404-13-0008). The government has certain rights in the invention.

SEQUENCE LISTING SUBMISSION VIA EFS-WEB

A computer readable text file, entitled "SequenceListing.txt," created on or about Dec. 30, 2020 with a file size of about 33,826 bytes contains the sequence listing for this application and is hereby incorporated by reference in its entirety.

BACKGROUND OF THE INVENTION

Macrophages are immune cells derived from monocytes that play an important role in host defense. Impaired macrophage responses have been observed in a number of debilitating genetic diseases. These diseases are difficult to study, however, because primary monocytes and macrophages obtained from patients do not live very long and are difficult to work with, and the availability of primary monocytes/macrophages is limited by the amount of blood that can be drawn from an individual patient. Likewise, there are very few immortalized monocyte/macrophage cell lines. Most existing lines are derived from tumors rather than true monocytes or macrophages, and none are from subjects with macrophage-centric immunodeficiencies. Thus, it would be highly desirable to have a means of efficiently immortalizing macrophages.

Previously, murine macrophage from fresh bone marrow were immortalized using the J2 virus, which expresses the v-raf and v-myc oncogenes. Blasi (1985) Nature 318:667. However, despite the longstanding need for a method of producing immortalized macrophage cell lines, J2 has not been widely adopted as a reagent for generating macrophage cell lines because it poses safety risks as a replicating and infectious virus. Further limitations of the J2 method for monocyte/macrophage immortalization are that the J2 virus is only capable of infecting mouse cells, the method for producing J2 virus involves a messy co-culture with a viral producer line, and the method for producing immortalized macrophage with the J2 virus uses monocytes obtained from bone marrow.

SUMMARY OF THE INVENTION

The present disclosure relates to a novel system for immortalizing mammalian cells, including monocytes and macrophages, by transducing them with a replication deficient virus that express the v-raf and v-myc oncogenes and, in some embodiments, a cell surface marker that can be used to identify and track transduced cells. The disclosure includes replication deficient viral vectors, host cells that produce replication deficient virus, methods of immortalizing mammalian cells such as monocytes and macrophages with a replication deficient virus, immortalized monocytes and macrophage cells, and methods of detecting an immortalized monocyte or macrophage.

In some embodiments, the viral vectors are lentiviral vectors pseudotyped with a vesicular stomatitis virus glycoprotein (VSV-G) that mediates infection of a broad range of species and cell types. The v-raf and v-myc oncogenes may be expressed independently or from a bicistronic vector. Alternatively, a multicistronic vector may be used in embodiments further comprising a cell surface marker. The individual genes of a bicistronic or multicistronic vector may be separated by self-cleaving linkers and/or internal ribosome entry sites.

The viral vectors are transformed into a host cell that produces the replication deficient virus. The host cell may be a HEK-293T cell to increase the yield of replication deficient virus. The virus produced by the host cell is used to transduce the oncogenes and optional cell surface marker into a mammalian cell, which is immortalized when the oncogenes are expressed. The cell transduced by the replication deficient virus is typically a monocyte or macrophage, and can be obtained from blood (a peripheral blood mononuclear cells), from the spleen (a splenocyte) or from bone marrow. Monocytes and macrophage can be isolated from any mammalian species, including a mouse, a ferret, a pig, or a human.

Immortalized macrophage cell lines may be produced by transducing a monocyte or macrophage with a replication-deficient virus that drives expression of v-raf, v-myc, and, optionally, a surface marker such as Thy1.1. After transduction, the cells are grown in media comprising granulocyte-monocyte colony stimulating factor (GM-CSF) for about 10 days. The GM-CSF is then removed, and the cells adhere to the surface of a culture dish. Cytodex beads are then added, and cells start proliferating on the surface of the bead. The resulting immortalized cells have the appearance and function of macrophage. They express mature macrophage surface markers (F4-80$^+$CD11b$^+$) and do not express markers found only on myeloid progenitor cells (Sca1 and c-kit). Like macrophages, they are capable of phagocytosis, and respond to gamma interferon ($\gamma$-IFN) by upregulating MHC II expression.

The replication-deficient viral vectors and methods of producing immortalized macrophage of the present invention have significant advantages when compared to prior vectors and methods. The new vectors are safer to use because they are replication deficient, and the new methods use viral supernatants for infection instead of a "messy" co-culture with a viral producer cell line. The new vectors have a more compact genome that provides an increase in viral yield, and efficiently produce the v-raf and v-myc oncogenes on a single mRNA transcript with a self-cleaving peptide. In contrast, it is unclear how the v-myc gene of the J2 virus can be expressed, as it is situated downstream of the v-raf gene and does not have any known regulatory sequences. This increased yield with the new vectors and methods allows transduction and successful cell line production to be performed with as few as 1×10$^5$ peripheral blood mononuclear cells (PBMCs). Immortalized macrophage can be produced from readily available blood cells, so a painful and invasive bone marrow aspiration is not required. The VSV-G pseudotyped lentiviral vector allows the method to be performed on blood from a broad range of mammalian species, including ferrets, pigs and humans, whereas the J2 virus could only transduce mouse cells. The cytokine independence of the resulting macrophage further facilitates use of the method in a broad range of mammalian species, including species without commercially available growth factors. Finally, the availability of a surface marker such as Thy1.1, that is recognized by a widely available antibody, allows infected cells to be traced over time (by flow cytometry or microscopy) and specifically isolated (e.g., by flow cytometry or bead-based sorting).

BRIEF DESCRIPTION OF THE DRAWINGS

The present application can be better understood by reference to the following drawings. The drawings are merely exemplary to illustrate certain features that may be used singularly or in any combination with other features and the present application should not be limited to the embodiments shown.

FIG. 1A-B. Identification of the p30 capsid region of MMLV-Gag included in LIVeMac constructs. (FIG. 1A) Cleavage products of the Gag polyprotein. (FIG. 1B) MMLV-Gag sequence with shading to indicate the p30 capsid region of Gag included in Gag-vRaf fusion for LIVeMac constructs (SEQ ID NO: 6). The sequence presented in this figure is from UniProt and is presented for illustrative purposes only. It differs slightly from the Gag-p30 sequence in LIVeMac, as not all MMLV isolates are identical.

FIG. 2. The Gag-vRaf junction of all LIVeMac constructs (SEQ ID NO: 8 & 9).

FIG. 3. The vRaf-T2A-vMyc junction of all LIVeMac constructs (SEQ ID NO: 10 & 11).

FIG. 5. The Thy1.1-P2A-p30Gag-vRaf junction region of LIVeMac-Thy1.1-N (SEQ ID NO: 12 & 13).

FIGS. 9A-C. Macrophage immortalized with LIVeMac. Images were taken 38 days ex vivo (34 days post-transduction). (FIG. 9A) 40× image of cells adherent to Cytodex 1 beads and cells adherent to the bottom of a tissue culture plate. The cells on beads are rounded; the cells on the plate look like macrophage. (FIG. 9B) 100× image of Cytodex 1 beads with cell colonies growing on their surface. At day 38, the cells require contact with the bead for cell division. (FIG. 9C) 100× image of cells adherent to plate. These cells do not replicate but begin to take on the appearance of phagocytic cells.

DETAILED DESCRIPTION OF THE INVENTION

Figure 4:
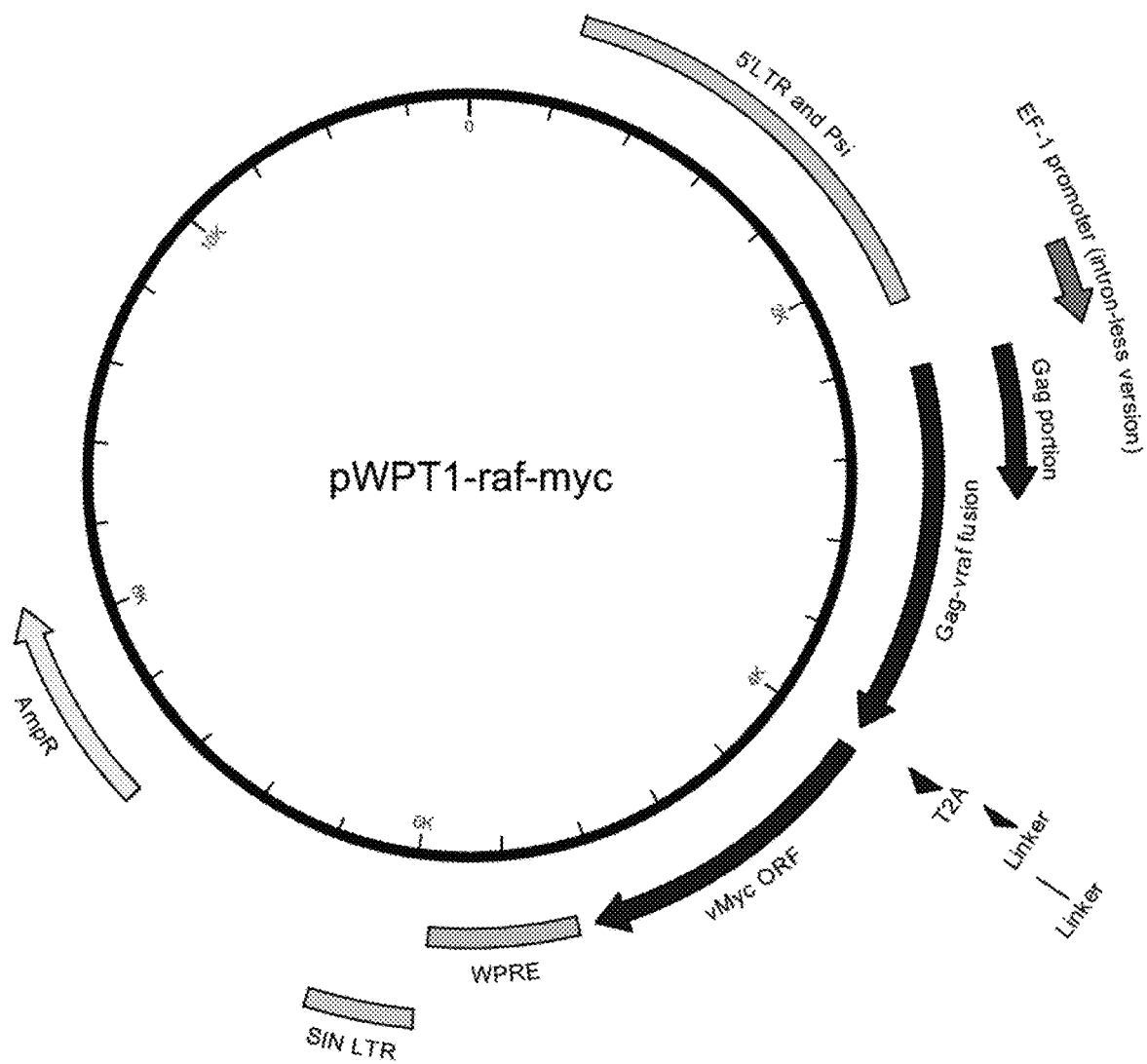
FIG. 4. Map of LIVeMac (untagged version).

The following detailed description is presented to enable any person skilled in the art to make and use the object of this application. For purposes of explanation, specific nomenclature is set forth to provide a thorough understanding of the present application. However, it will be apparent to one skilled in the art that these specific details are not required to practice the subject of this application. This description is intended to be read in connection with the accompanying drawings, which are to be considered part of the entire written description of this application. Descriptions of specific applications are provided only as representative examples. The present application is not intended to be limited to the embodiments shown, but is to be accorded the widest possible scope consistent with the principles and features disclosed herein.

One aspect of the present disclosure relates to a replication-deficient viral vector for immortalizing mammalian cells comprising, a polynucleotide encoding a v-raf protein comprising a sequence having at least 95% identity to SEQ ID NO: 4 and a polynucleotide encoding a v-myc protein comprising a sequence having at least 95% identity to SEQ ID NO: 5.

In some embodiments, the v-raf and v-myc proteins are expressed from a single bicistronic or multicistronic mRNA transcript and separated by a 2A self-cleaving linker.

In some embodiments, the vector comprises a promoter that is an EF1a promoter or another suitable promoter.

In some embodiments, the replication-deficient viral vector further comprises a polynucleotide encoding a surface marker.

In some embodiments, the surface marker is a thy1.1 protein comprising a sequence having at least 95% identity to SEQ ID NO: 6. In some further embodiments, the polynucleotide encoding the thy1.1 protein is operatively linked to an internal ribosome entry site.

In some embodiments, the thy1.1 protein is expressed from a multicistronic mRNA transcript and separated from the v-raf and v-myc proteins by a 2A self-cleaving linker.

In other embodiments, the surface marker is an NGFR or an epitope-tagged version of any desired surface protein.

In some embodiments, the replication-deficient viral vector further comprises a polynucleotide encoding a fluorescent protein including, but not limited to, GFP, dsRed, CFP, or YFP.

In some embodiments, the replication-deficient viral vector further comprises a polynucleotide encoding a drug-selectable marker.

In some embodiments, the replication-deficient viral vector further comprises a polynucleotide encoding a VSV-G envelope glycoprotein comprising a sequence having at least 95% identity to SEQ ID NO: 7.

In some embodiments, the vector is a lentiviral vector. In some embodiments, the lentiviral vector comprises nucleic acids derived from a J2 virus.

In some embodiments, the replication-deficient viral vector comprises a polynucleotide encoding the p30Gag-vRaf-T2A-vMyc fusion protein of SEQ ID NO: 1. In some embodiments, the replication-deficient viral vector comprises a polynucleotide encoding (a) the Thy1.1 protein of SEQ ID NO: 3 and the p30Gag-vRaf-T2A-vMyc fusion protein of SEQ ID NO: 1, or (b) the Thy1.1-P2A-p30Gag-vRaf-T2A-vMyc fusion protein of SEQ ID NO: 2.

Another aspect of the present disclosure relates to a host cell comprising the replication-deficient virus as described herein. In some embodiments, the cell is a HEK-293T cell.

Another aspect of the present disclosure relates to a replication deficient virus produced by a host cell as described herein.

Another aspect of the present disclosure relates to a method of immortalizing a mammalian cell comprising contacting the cell with the replication-deficient virus as described herein.

In some embodiments, the mammalian cell is inclusive of, but not limited to, mouse, rat, ferret, pig and human.

In some embodiments, the mammalian cell is a monocyte, a macrophage or a related cell. In some further embodiments, the monocyte, macrophage or related cell is a peripheral blood mononuclear cell. In other further embodiments, the monocyte, macrophage or related cell is a splenocyte.

In some embodiments, the macrophage or related cell is inclusive of, but not limited to, microglia, Kupffer cells, alveolar macrophages, Langerhans cells, adipose tissue macrophages, osteoclasts, tumor associated macrophages, and dendritic cells.

Another aspect of the present disclosure relates to a method of differentiating the immortalized monocyte as described herein into a macrophage comprising, (a) proliferatively growing the monocytic cell, (b) growing the monocytic cell on a solid surface, and (c) growing the monocytic cell on a porous surface. In some embodiments, the porous surface is a dextran-based bead.

Another aspect of the present disclosure relates to an immortalized macrophage produced by the method described herein. In some embodiments, the immortalized macrophage (a) expresses a surface protein characteristic of a macrophage, and (b) does not express a surface protein characteristic of an undifferentiated monocyte progenitor cell. In some embodiments, the macrophage has phagocytic activity. In some embodiments, the macrophage responds to treatment with γ-interferon by upregulating expression of an MHC II gene.

Another aspect of the present disclosure relates to a method of detecting the immortalized monocyte produced by the method described herein or the immortalized macrophage as described herein by contacting the immortalized monocyte or immortalized macrophage with a reagent having specific affinity for the surface marker as described herein. In some embodiments, the reagent is a fluorescently-labeled antibody having specific affinity for thy1.1.

Defects in macrophage function play a major role human genetic diseases. Immortalization of macrophages from individuals with macrophage defects could be used to screen drug libraries or to elucidate the basis of disease and develop novel therapeutics.

Such diseases include lipid storage diseases, such as (but not limited to) Gaucher disease or Niemann-Pick disease; diseases characterized by defects in macrophage activation, such as (but not limited to) anhidrotic ectodermal dysplasia with immune deficiency (EDA-ID), IL-12 or IL-12 receptor deficiency, interferon (IFN)-gamma deficiency, or STAT-1 deficiency; immunodeficiencies affecting phagocyte functions such as (but not limited to) chronic granulomatous disease and myeloperoxidase deficiency.

Immortalized macrophages of the present disclosure would also provide benefits in regard to diseases characterized by defects in phagocyte function (although impairment of neutrophil function receives the most attention, these immunodeficiencies also affect macrophage phagocytic function, and immortalized macrophages from such patients would thus be an important resource to study these diseases) including, but not limited to, chronic granulomatous disease or myeloperoxidase deficiency.

Immortalized macrophages of the present disclosure can be used in studies involving infectious diseases and are particularly applicable to pathogens which are tropic for myeloid cells including (but not limited to) *Mycobacterium tuberculosis* and other mycobacterial species; *Yersina* species, and *Salmonella* species.

There are also many other diseases in which macrophages are known or suspected play a major role (atherosclerosis, cancer, Lupus, rheumatoid arthritis), and immortalized macrophages from individuals with these diseases may be useful to elucidate defects in macrophage function that contribute to pathology.

In mice, LIVeMac can be used to immortalize macrophages from genetically distinct specimens (i.e. knockout vs wild type or species A vs species B). The resulting cell lines will allow researchers to investigate a particular gene or mutation without having to repeatedly harvest primary cells.

At the same time, this platform provides consistent background (cells were immortalized the same way) reducing the number of variables involved in the experiment. Rare genetic mutations affecting macrophages and which cause disease or cancer can be studied indefinitely.

Macrophage cell lines created using LIVeMac could also likely be used to create cell lines lacking expression of desired target genes by CRISPR or similar techniques.

Another aspect of the present disclosure relates to use of the immortalized macrophages to produce certain biologicals, particularly those normally produced in relatively large amounts by macrophages—cytokines are the most obvious potential product (e.g., IL-6, TNF-a, IFN-g), but production of other mediators normally produced in high quantities by macrophages (e.g., galectin-3) would also be possible.

Another aspect of the present disclosure relates to polynucleotides encoding polypeptides having at least 95% identity to a v-raf protein, a v-myc protein, and/or a thy1.1 protein. The similarity or identity of amino acid sequences, i.e. the percentage of sequence identity, can be determined via sequence alignments. Such alignments can be carried out with several art-known algorithms, such as with the mathematical algorithm of Karlin and Altschul (Karlin & Altschul (1993) Proc. Natl. Acad. Sci. USA 90: 5873-5877), with hmmalign (HMMER package, hmmer.wustl.edu/) or with the CLUSTAL algorithm (Thompson (1994) Nucleic Acids Res. 22, 4673-80). The grade of sequence identity (sequence matching) may be calculated using e.g. BLAST, BLAT or BlastZ (or BlastX). A similar algorithm is incorporated into the BLASTP programs of Altschul (1990) J. Mol. Biol. 215: 403-410. BLAST protein searches may be performed with the BLASTP program, score=50, word length=3. To obtain gapped alignments for comparative purposes, Gapped BLAST is utilized as described in Altschul (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno (2003) Bioinformatics, 19 Suppl 1:154-162) or Markov random fields.

Changes to the amino acid sequence of a polypeptide can alter its function or have no measurable effect. Silent changes with no measurable effect are most likely to be conservative substitutions and small insertions or deletions on solvent-exposed surfaces that are located away from active sites and substrate-binding sites. In contrast, function is more likely to be affected by non-conservative substitutions, large insertions or deletions, and changes within active sites, substrate-binding sites, and at buried positions important for protein folding or conformation. Changes that alter protein function may increase or decrease reaction rates or binding affinities. For example, changes that increase the size of a substrate-binding site may permit an enzyme to act on larger substrates and changes that position a catalytic amino acid side chain closer to a target site on a substrate may increase the enzymatic rate.

A substitution is the replacement within a polypeptide of a new amino acid residue for an old one. In a conservative substitution, the old and new amino acids have similar characteristics such as size and charge. Naturally occurring residues are divided into groups based on common side chain properties:

(group 1) hydrophobic (aliphatic): methionine (Met), Alanine (Ala), Valine (Val), Leucine (Leu), Isoleucine (Ile)
(group 2) neutral hydrophilic: Cysteine (Cys), Serine (Ser), Threonine (Thr)
(group 3) acidic: Aspartic acid (Asp), Glutamic acid (Glu)
(group 4) basic: Asparagine (Asn), Glutamine (Gln), Histidine (His), Lysine (Lys), Arginine (Arg)
(group 5) residues that influence chain orientation: Glycine (Gly), Proline (Pro); and
(group 6) aromatic: Tryptophan (Trp), Tyrosine (Tyr), Phenylalanine (Phe)

Non-conservative substitutions will entail exchanging a member of one of these classes for another.

Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Me, and Leu are interchangeable but because of size Gly and Ala are more closely related and Val, lie and Leu are more closely related to each other, and the aromatic amino acids Phe, Trp and Tyr may be interchangeable.

Extensive structure-function studies on v-raf, v-myc, and thy1 provide guidance on changes that can be made to their amino acid sequences without destroying their functions. See Wellbrock (2004) Nat. Rev. Mol. Cell. Biol. 5:875-85; Leicht (2007) Biochim Biophys Acta, 1773: 1196-1212; Meyer (2008) Nature Reviews Cancer 8:976-990; Mansour (2004) J. Immunol. 173:3581-3588; Kuhn (2002) Proteins. 49:142-5.

Viral vectors provide an efficient means for modification of eukaryotic cells and their use is now commonplace in academic laboratories and industry for both research and clinical gene therapy applications. Lentiviral vectors, derived from the human immunodeficiency virus, have been extensively investigated and optimized over the past two decades. Lentiviral vectors offer several attractive properties as gene-delivery vehicles, including: (i) sustained gene delivery through stable vector integration into host genome; (ii) the capability of infecting both dividing and non-dividing cells; (iii) broad tissue tropisms, including important gene- and cell-therapy-target cell types; (iv) no expression of viral proteins after vector transduction; (v) the ability to deliver complex genetic elements, such as polycistronic or intron-containing sequences; (vi) potentially safer integration site profile; and (vii) a relatively easy system for vector manipulation and production. Sakuma T. et al., Lentiviral vectors: basic to translational, Biochem J. 2012 May 1; 443(3):603-18. Self-inactivating lentiviral vectors were developed for improved safety. Third-generation lentiviral vectors require three helper plasmids in addition to the plasmid carrying the transgene. All accessory genes of HIV-1 (vif, vpr, vpu, and nef) have been removed because they are not necessary. Merten (2016) Mol. Ther. Methods Clin. Dev. 3:16017.

The host range of retroviral vectors including lentiviral vectors can be expanded or altered by a process known as pseudotyping. Pseudotyped lentiviral vectors consist of vector particles bearing glycoproteins derived from other enveloped viruses. Such particles possess the tropism of the virus from which the glycoprotein was derived. Among the first and still most widely used glycoproteins for pseudotyping lentiviral vectors is the vesicular stomatitis virus glycoproteins (VSV-G), due to the very broad tropism and stability of the resulting pseudotypes. Cronin (2005) Curr. Gene Ther. 5:387-398.

Co-expression of multiple genes at a desired ratio is highly attractive for a broad array of basic research and biomedical applications including cellular reprogramming, expression of multiple subunits of complex multimeric proteins in gene therapy, tagging of protein of interest for live cell imaging or cell sorting, and generation of efficient tools for fate mapping and genome editing. Strategies for multigene co-expression include introduction of multiple vectors, use of multiple promoters in a single vector, fusion proteins, proteolytic cleavage sites between genes, internal ribosome entry sites, and "self-cleaving" 2A peptides. 2A peptides are 18-22 amino-acid (aa)-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (thosea asigna virus 2A) were also identified. The mechanism of 2A-mediated "self-cleavage" was recently discovered to be ribosome skipping the formation of a glycyl-prolyl peptide bond at the C-terminus of the 2A. A highly conserved sequence GDVEXNPGP is shared by different 2As at the C-terminus, and is essential for the creation of steric hindrance and ribosome skipping. 2A peptides lead to relatively high levels of downstream protein expression compared to other strategies for multi-gene co-expression, and they are small in size thus bearing a lower risk of interfering with the function of co-expressed genes. 2A peptides have been successfully employed for polycistronic and bi-cistronic multigene expression. Liu (2017) Sci. Rep. 7:2193.

The present invention is further illustrated by the following examples which should not be construed as limiting. The contents of all references, patents and published patent applications cited throughout this application, as well as the Figures, are incorporated herein by reference.

EXAMPLES

Example 1: Construction of LIVeMac Plasmids

Lentiviral vectors constructed for the purpose of producing immortalized macrophages are referred to as LIVeMac (Lentivirus Immortalizing Vertebrate Macrophages) plasmids, and have bicistronic or multicistronic inserts.

The v-raf and v-myc oncogenes were isolated by PCR from the J2 plasmid (Rapp (1985) Virology 55:23-33; Blasi (1985) Nature 318:667-70). The v-raf gene of J2 is part of a MMLV-Gag/v-raf fusion. The Gag portion of this polyprotein is likely to be cleaved in J2-infected cells, as illustrated in FIG. 1A. To reduce the length of DNA inserted into the lentiviral vector, which should increase transformation efficiency and viral yields, DNA encoding the Matrix protein (p15) and RNA-binding phosphoprotein (p12) was excluded from the PCR product and replaced with an initiator methionine. The resulting Gag/v-raf fusion contained only the shaded region of Gag shown in FIG. 1B. The Gag-p30/ v-raf fusion site at position 384 of the Gag polyprotein is identical to the corresponding region of J2, and does not include the nucleocapsid protein (p10). This modified Gag-v-Raf was amplified by PCR using a primer encoding the self-cleaving T2A peptide and inserted into the pBluescript-KS+ vector (pBS), yielding pBS-v-Raf-T2A.

After confirming the sequence of pBS-v-Raf-T2A, the v-myc gene of J2 was inserted downstream of T2A, in the same reading frame, as illustrated in FIG. 3. In this manner, both v-Raf and v-Myc are produced as a single open reading frame (ORF) that is co-translationally cleaved into v-Raf and v-Myc components by the inherent self-cleaving activity of the T2A peptide sequence. This plasmid was called pBS-v-Raf-T2A-v-Myc.

The v-Raf-T2A-v-Myc portion was subcloned into the $2^{nd}$-generation self-inactivating lentiviral vector, pWPT, to generate pWPT-v-Raf-T2A-v-Myc, also known as LIVeMac. FIG. 4. pWPT has a self-inactivating 3' LTR, which results in inactivation of the 5'LTR upon reverse transcription. Consequently, an internal EF-1 promoter drives transcription of inserted genes. The pWPT portion of this construct was obtained as a pWPT-GFP plasmid. The GFP gene was replaced with a polylinker sequence, and v-Raf-T2A-v-Myc was then inserted into the polylinker. SEQ ID NO: 1 shows the amino acid sequence of the p30Gag-vRaf-T2A-vMyc fusion protein of LIVeMac.

Figure 6:
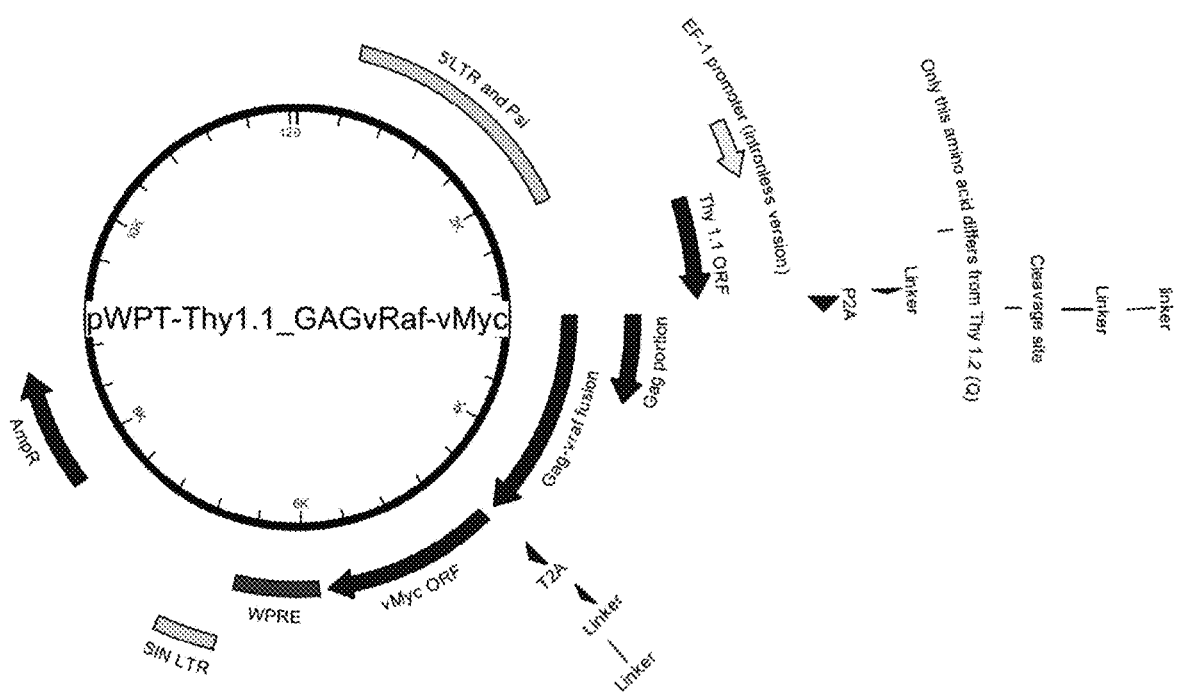
FIG. 6. Map of LIVeMac-Thy1.1-v1.

LIVeMac-Thy1.1-v1 has a Thy1.1 marker inserted at the 5' end of the Gag/v-raf fusion, which is separated from Gag/v-raf by a P2A self-cleaving peptide. FIG. 5 presents the sequence of the junction with the P2A linker, and FIG. 6 is a map of the entire LIVeMac-Thy1.1-v1 plasmid. To construct LIVeMac-Thy1.1-v1, the full expression cassette was first assembled in in pBS (yielding pBS-Thy1.1-P2A-v-Raf-T2A-v-Myc), followed by subcloning into pWTP. LIVeMac-Thy1.1-v1 expresses a Thy1.1-vRaf-vMyc polyprotein with two self-cleaving sites, yielding separate Thy1.1, v-Raf, and v-Myc components. SEQ ID NO: 2 shows the amino acid sequence of the Thy1.1-P2A-p30Gag-vRaf-T2A-vMyc fusion protein of LIVeMac-Thy1.1-v1.

Figure 7:
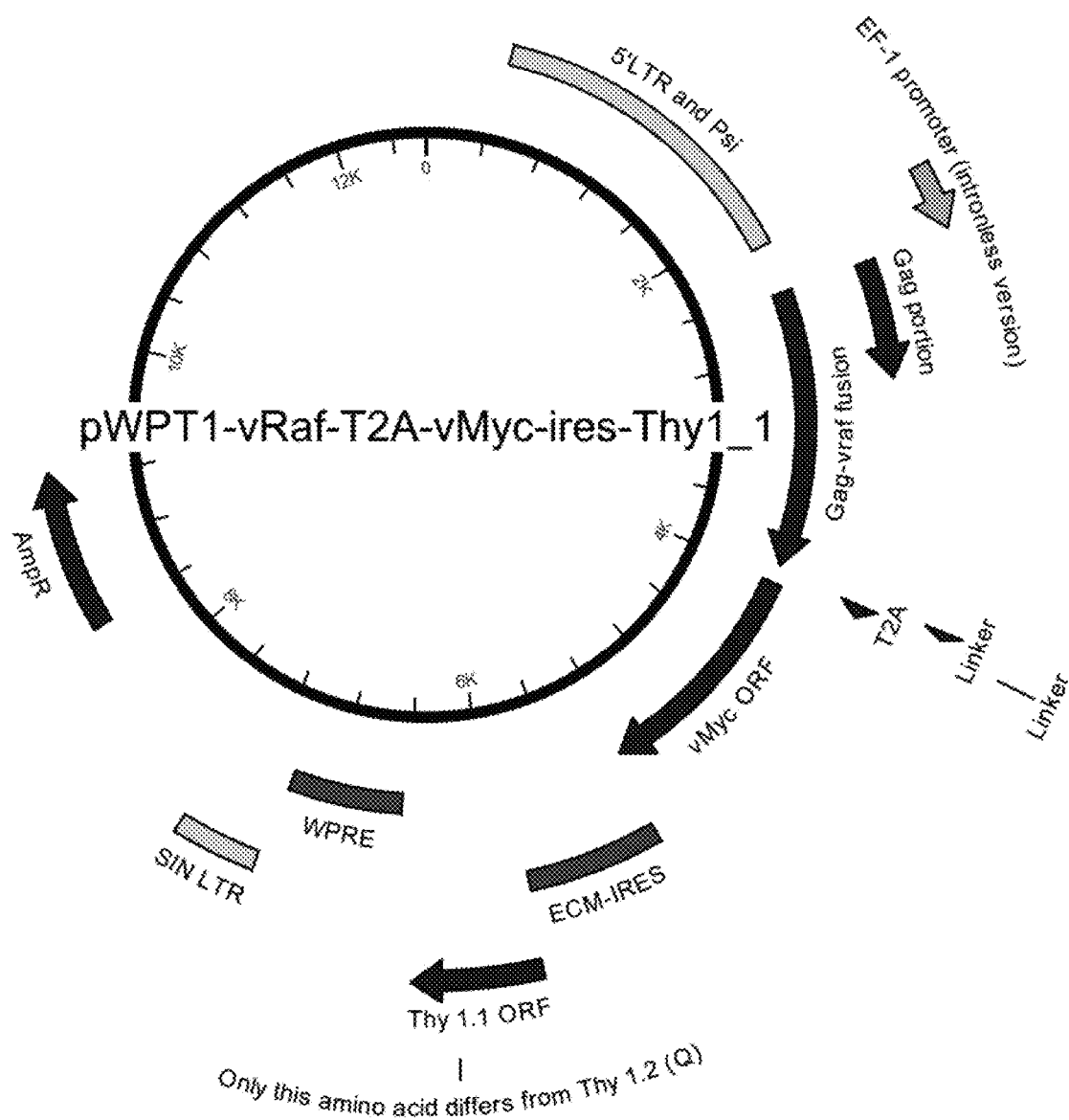
FIG. 7. Map of LIVeMac-Thy1.1-v2.

LIVeMac-Thy1.1-v2 has a Thy1.1 marker inserted with an internal ribosome entry site (IRES) at the 3' end of the Gag/v-raf fusion. FIG. 7. To construct LIVeMac-Thy1.1-v2, v-Raf-T2A-v-Myc was inserted upstream of an IRES-Thy1.1 cassette in the vector pSP72. This cassette was then subcloned into pWPT, yielding pWPT-v-Raf-T2A-v-Myc-IRES-Thy1.1, also known as LIVeMac-Thy1.1-v2. In this construct, the Thy1.1 cassette is produced from the same primary viral RNA transcript as a separate ORF, via internal ribosome binding at the IRES. SEQ ID NO: 3 shows the amino acid sequence of the Thy1.1 polypeptide of LIVeMac-Thy1.1-v2. LIVeMac-Thy1.1-v2 also expresses the p30Gag-vRaf-T2A-vMyc fusion protein of SEQ ID NO: 1.

Example 2: Production of Viral Supernatants

LIVeMac vectors were used to produce virus by employing a $2^{nd}$-generation lentiviral packaging system. LIVeMac plasmid DNA was co-transfected into HEK-293T cells with a plasmid encoding the vesicular stomatitis virus glycoprotein (VSV-G) and the packaging plasmid, pCMV-R8.74, which encodes lentivirus structural proteins. The resulting supernatants contain infectious, replication-incompetent VSV-G-pseudotyped lentiviral particles.

The transfection protocol used, as follows, is a modified version of that described by Jordan (1996) Nucl. Acids. Res. 24:596-601.

Day 1

Afternoon before transfection, split cells (HEK-293T or the Phoenix packaging line) so that they will be 50-80% confluent in 24 hours. Split cells into a 6 well plate in 1 ml of complete media (DME works well, RPMI does not work well), and grow cells in 37° C., 5% $CO_2$ incubator. Plating $6\times10^5$ per well gives the appropriate density. Note: it is also worthwhile to pretreat wells with 100 μg/ml poly-D-lysine (Sigma P-0899) in dd$H_2O$ (5 minutes, room temp). Wash wells 2× with sterile 1×BSS or 1×PBS before plating cells. This treatment will prevent cell loss during the media change on Day 3.

Day 2

1. Warm to 37° C. the appropriate volume of Iscove's Modified Dulbecco's Medium (IMDM supplemented with antibiotics and 10% fetal bovine serum) enough to provide 1.5 mL per well to be transfected. Replace the DMEM with 1.5 mL pre-warmed IMDM. Note: It is important to use IMDM—this will increase the transfection efficiency from 30-50% to 100%.

2. For each well of a 6-well plate to be transfected, assemble the following in a sterile 1.5 mL tube: add 1.7 μg of Qiagen- or CsCl-purified lentiviral plasmid DNA (e.g., pWPT-GFP), 0.8 μg of the packaging plasmid pCMV-R8.74 and 0.5 μg of the pMD2. G envelope plasmid to 7.5 μl of 2.5 M $CaCl_2$. Add sterile dd$H_2O$ to a final volume of 75 μl. Prepare all DNA samples to be used in transfections before proceeding to Step 2. Note: The ratio of lentiviral DNA: packaging DNA: envelope DNA is consistent with a posted web protocol: lentiweb.com/protocols_lentivectors.php. Empirical optimization may yield improved results in your hands. However, the DNA total should always be 3 μg.

3. Add 75 μl of 2×HEPES solution and pipet up and down 4× to mix.

4. After exactly 1 minute add the calcium-phosphate-DNA precipitate in dropwise fashion to one well of the cells in the six well plate. Distribute the 150 μl over as much of the surface of the media as possible (i.e., do not put the entire 150 μl in the center of the well). Note: You should be able to observe a very fine DNA precipitate using a 20× microscope objective. If the precipitate is not present or is composed primarily of large aggregates, check the pH of the 2×HEPES solution. Certain plasmids seem to have a tendency to form aggregates, so it may not be possible to eliminate aggregates in every case.

5. Repeat Steps 2 and 3 for each well to be transfected. When transfecting larger or small numbers of cells, adjust all volumes proportionally—thus, the final DNA concentration should be 3 µg/150 µl of 2×HEPES-calcium-phosphate transfection mix, and the final concentration of calcium in the media following addition of the transfection mix is approximately 12.5 mM.

Day 3

24 hours following addition of transfection mix, remove media, wash cells 2× with 2 mL of sterile 1×PBS or 1×BSS, then replace with 2 ml fresh complete media per well (e.g., DMEM+antibiotics and 10% fetal bovine serum). Note (1): 24 hours is the optimal time for the cells to be in the presence of the precipitated DNA. 2 mL of media is the optimal volume (maximal number of viral particles produced at the maximal concentration). Note (2): A simplified variation of this step, which eliminates the need to safely aspirate and discard lentivirus-containing supernatant, is to add 1.5 mL of complete DMEM to the existing 1.5 mL of IMDM already in the well. This variation reproducibly yields 3 mL of high-titer supernatant per transfected well.

Days 4 and 5

Harvest viral supernatant 24 hours after replacement of the media. A second harvest (with approximately 50% of the titer of the first) can be made 12-24 hours later—simply add another 2 mL of media, and return the plate to the incubator.

Other Factors

Effective viral titers may be increased by incubating cells at 32° C. (days 3-5).

Virus can also be concentrated by centrifugation (Ichim (2011) Translational Medicine 9:137; Zhang (2001) Gene Therapy 8:1745-1751).

Target cells can be spinfected: place cells in a tissue culture well with retroviral supernatant and polybrene at 10 µg/ml (more polybrene will give better infection frequency, but is toxic to certain cell types), spin in a swinging bucket rotor at 1000 g for 2 hours at room temp (use a ziploc bag to keep the $CO_2$ in the plate). Immediately following spinfection, replace supernatant with fresh media.

Retroviral supernatants can be frozen (−70° C.) with a 2× loss of titer. Do not refreeze after thawing. Supernatants can also be stored short term at 4° C. It takes approximately 2 weeks for a 50% loss of titer, although this rate may vary with media composition, etc. It would be best to test this empirically for each type of media to be used.

Solutions 2.5 M $CaCl_2$: 18.375 g $CaCl_2(2H_2O)$, MilliQ $H_2O$ to 50 ml, Filter Sterilize.

2×HEPES Solution: 14 ml 1 M NaCl (140 mM final); 0.5 ml 300 mM NaPhosphate (1.5 mM final); 5 ml 1M HEPES, pH 7.05 (50 mM final); pH to exactly 7.05; MilliQ $H_2O$ to 100 ml, Filter Sterilize.

300 mM NaPhosphate: 1.38 g $Na_2HPO_4$; 0.63 g $NaH_2PO_4$; MilliQ $H_2O$ to 50 ml.

1M HEPES, pH 7.05; 11.92 g HEPES Acid; pH to 7.05; MilliQ $H_2O$ to 50 ml.

Example 3: Immortalization of Peripheral Blood Mononuclear Cells with LIVeMac

Figure 8:
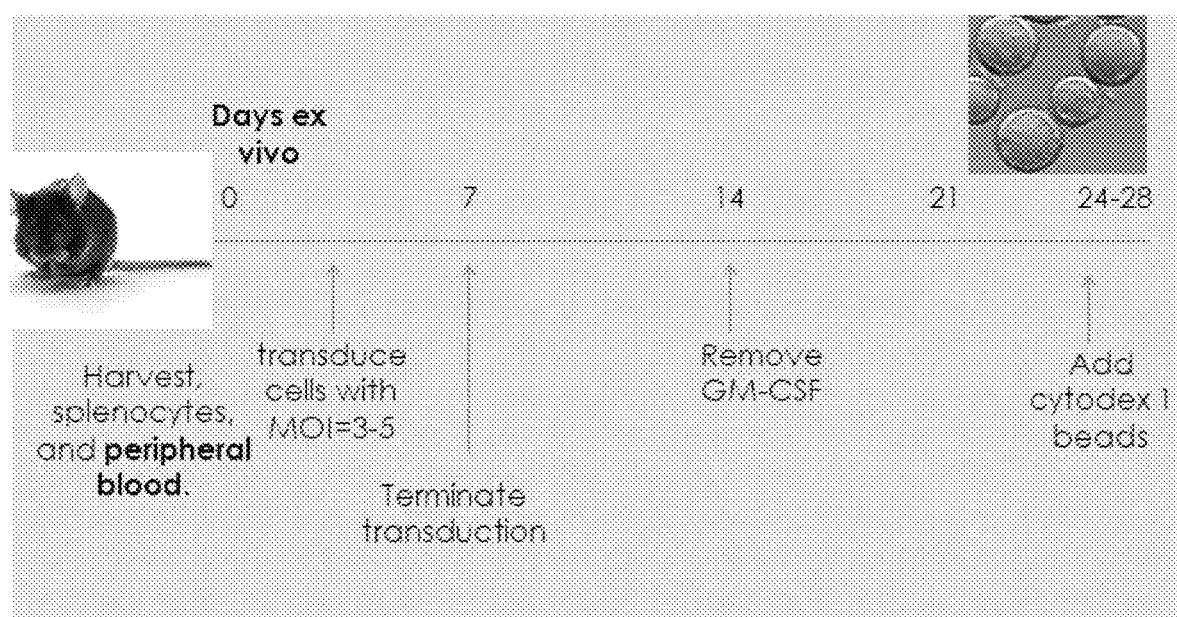
FIG. 8. Protocol for generating immortalized mouse macrophage.
Figure 10B:
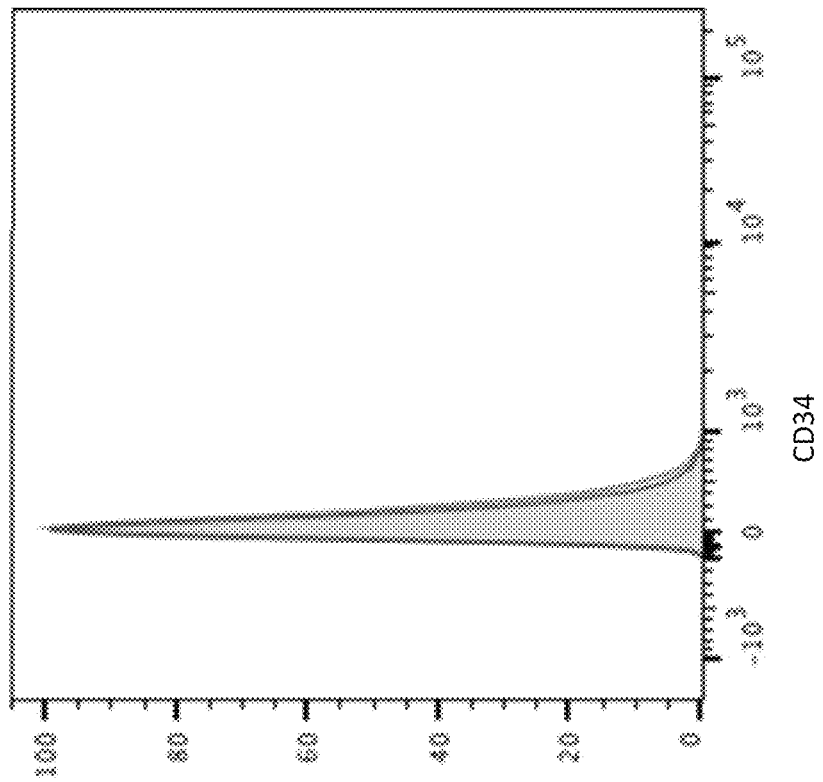
FIGS. 10A-I. Peripheral blood derived cells immortalized with LIVeMac display surface markers characteristic of mature macrophages, as determined by flow cytometry. No labeling was observed when staining for immature myeloid and progenitor markers (FIG. 10A) c-kit, (FIG. 10B) CD34, or (FIG. 10C) Flt3, or for granulocyte markers Siglec F (FIG. 10E), Ly6G (FIG. 10F) or Ly6C (FIG. 10G). Positive staining was observed for mature macrophage markers (FIG. 10D) CD11b and F4-80 (not shown; and see FIG. 11). F4-80 is a mouse marker for fully mature macrophage and is specific to this cell type. Staining for CD64 (FIG. 10H) and weak staining for CD11c (FIG. 10I) is also consistent with mature macrophages.
Figure 10A:
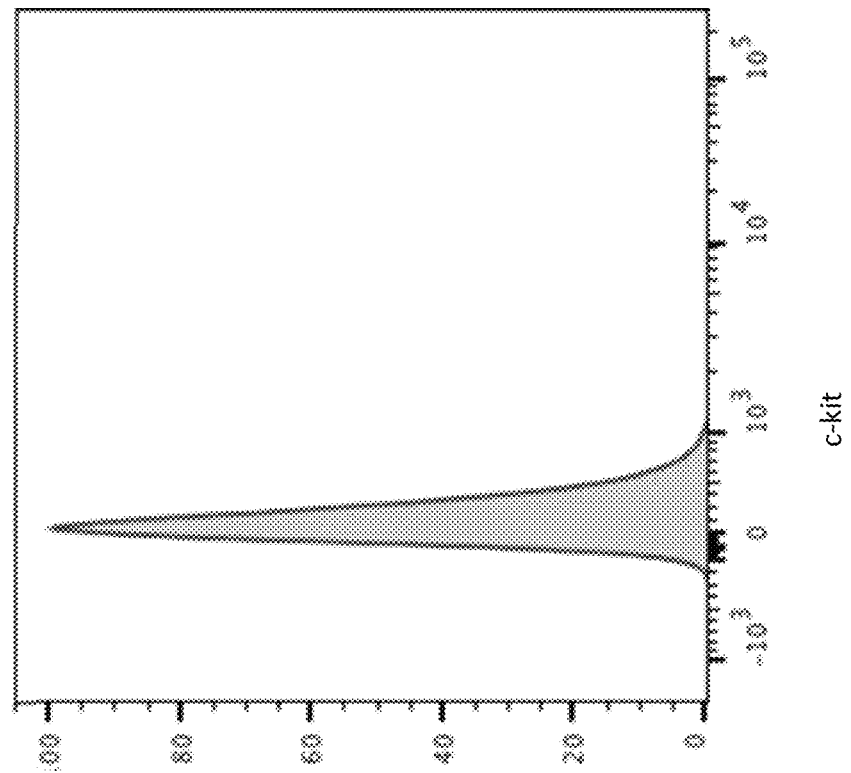
Figure 10D:
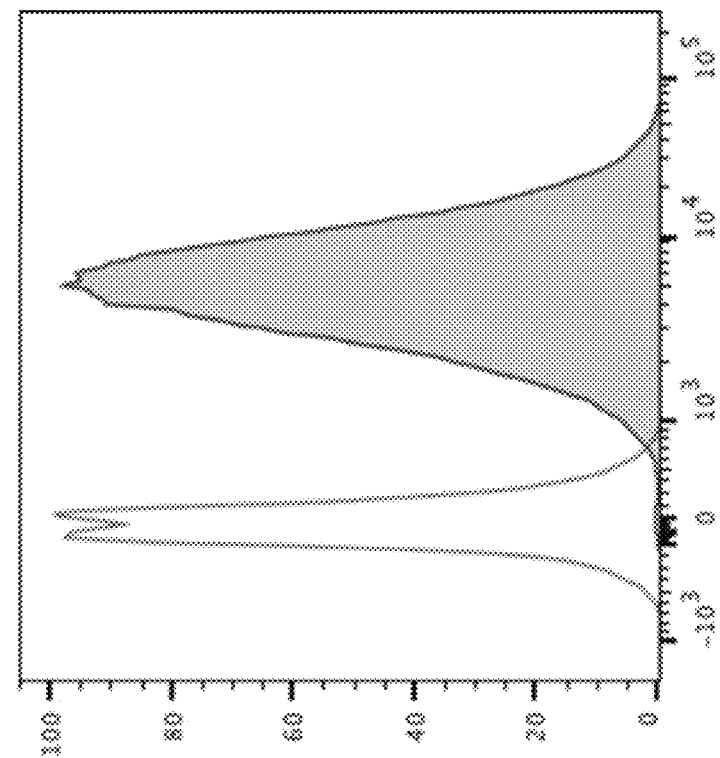
Figure 10C:
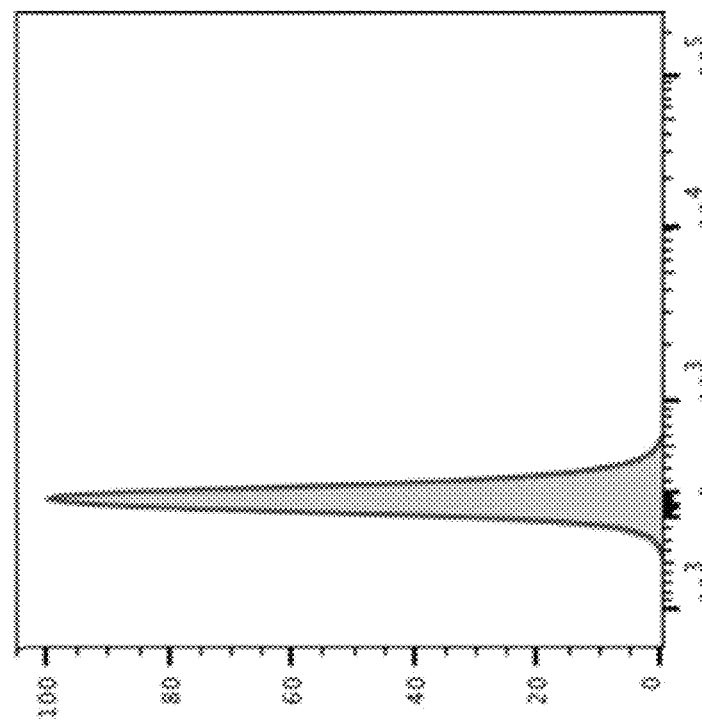
Figure 10E:
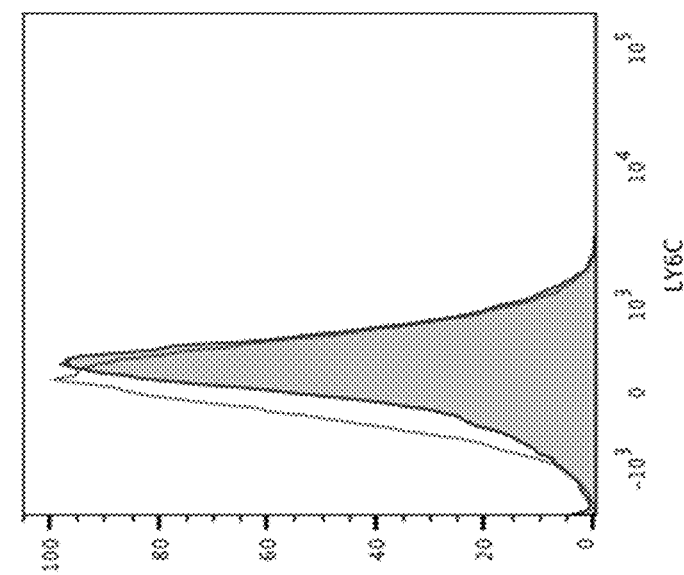
Figure 10F:
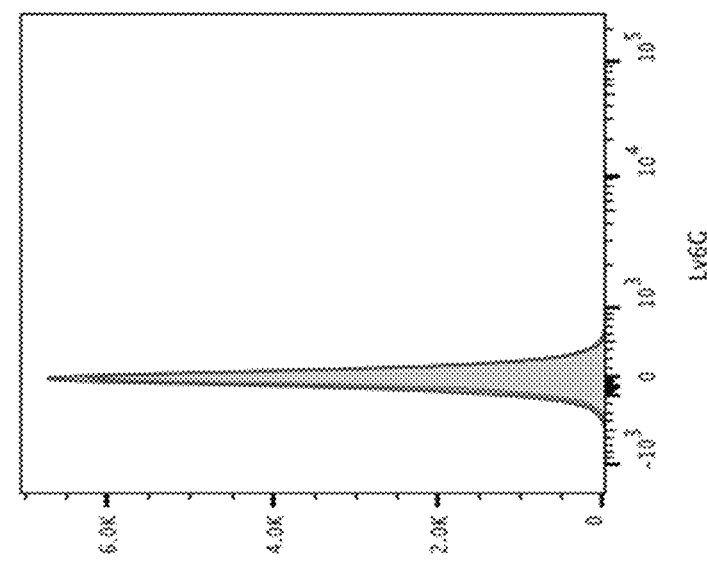
Figure 10G:
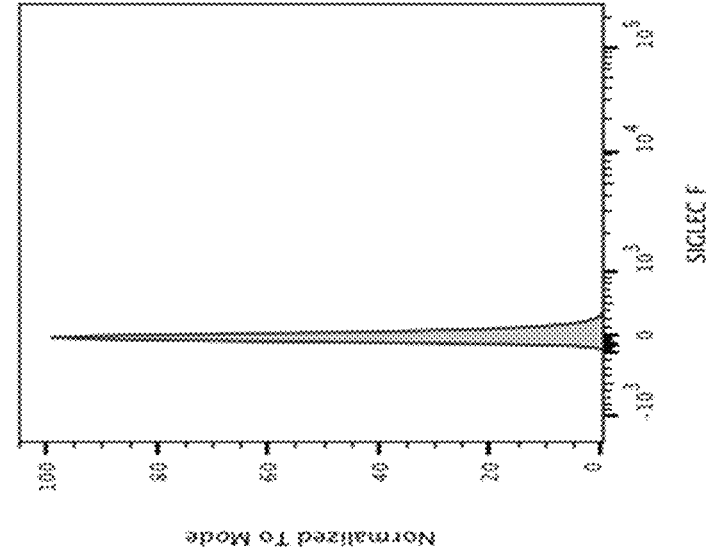
Figure 10I:
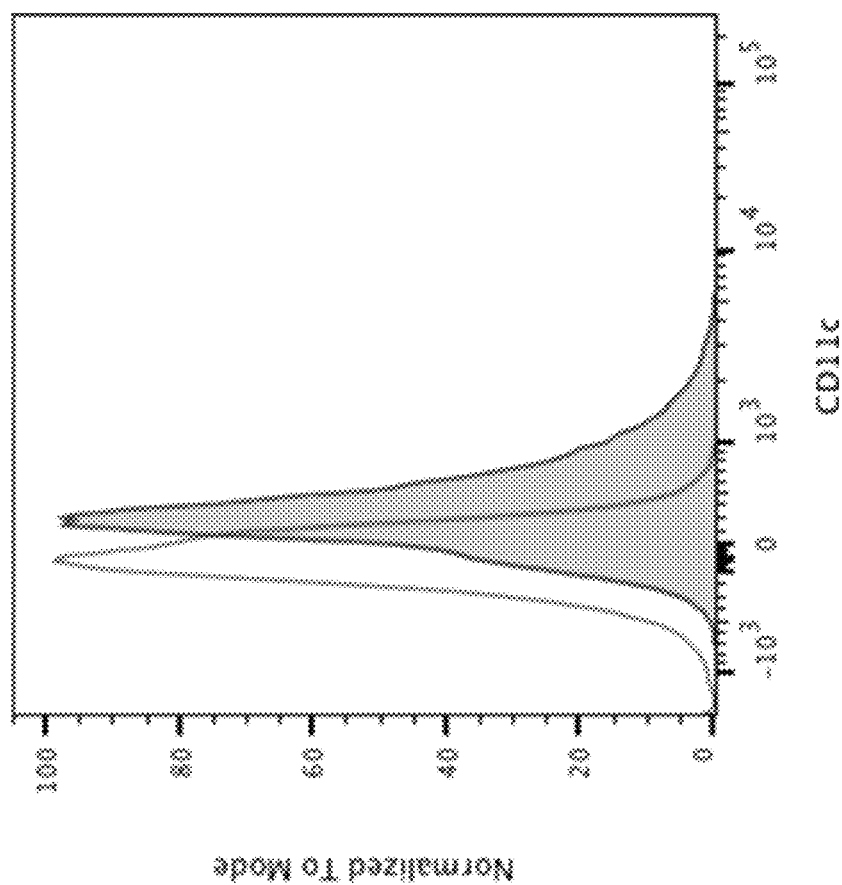
Figure 10H:
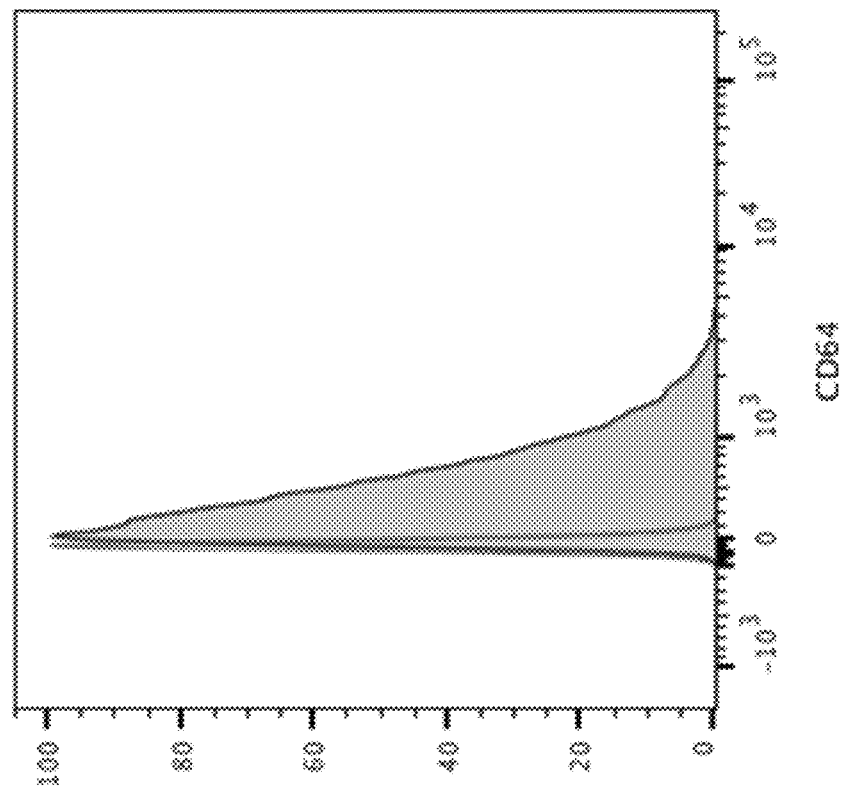

The overall procedure used for preparing immortalized macrophages from PBMCs is illustrated in FIG. 8. Prepare peripheral blood mononuclear cells according to standard protocols by, for example, lysing red blood cells and the collecting cells by density gradient centrifugation.

Culture collected cells in a petri plate or non-tissue treated 24 well plate in DMEM with 10% Cosmic Calf Serum, L-Glutamine, and Penicillin/streptomycin. The media should also contain GM-CSF from a feeder cell line at a concentration of 1×.

Cells should be left in this condition for 4 days. At this point myeloid cells should be proliferating and appear as colonies of round clustered cells. This is the optimal time to transduce the cells.

Coat plates that cells will be transduced in with Retronectin (a fibronectin fragment that binds retrovirus, enhancing infectivity) at 50 µg/mL per the company protocol.

Add viral supernatant containing LIVeMac to coated plates and spin at 1000 g for 90 minutes at 32° C. MOI of around at least 5 work best though lower can be used.

Incubate the plate at 32° C. for 2.5 hours then remove the supernatant and gently wash one time with PBS, without letting the well dry out.

Cells that have been in culture for four days were added to the well in ½ conditioned media (media the cells had been growing in) and ½ new media (same type as in step 2). As few as 100,000 cells can be plated in each well of a 24 well plate and still result in immortalized macrophages. Around 200,000-250,000 cells is ideal. Overcrowding of the wells, causes the cells to differentiate differently and does not result in immortalized macrophages.

Three days later, cells are removed using trypsin from the wells containing virus and washed 2× with PBS. Cell viability should be at around 80%-90% at this point and the cells should have about tripled in number.

At this point, cell proliferation should be finished or very slow. Seed the cells in a new non-tissue treated 24 well plate in all new DMEM with 1×GMCSF.

Seven days later you can wash the well with PBS to remove the dead cells and move the rest of them to a new well. Alternatively, you can leave them in the same well. At this point most cells will have died (presumably those that did not get infected with the virus) and lifting remaining cells risks losing even more cells.

At this point cells are cultured in DMEM without GM-CSF. The cells will adhere to the bottom of the plate and take on a particular morphology (See pictures below). They will be metabolically inactive. The media will not change color but the cells will remain adherent and look healthy.

Two weeks later, add 200 µg of cytodex 1 beads directly to the adherent cells in the wells, without lifting the cells first.

Cells will begin to adhere to the beads within a few days but will take about a week to see obvious replication.

Cells will continue expanding and can be split by taking cytodex beads with cells on them and moving them to wells with new beads.

Slowly decreasing the concentration of beads in the wells will eventually lead to cultures that no longer require the beads to replicate. Taking the beads away directly, however, will put the cells back in the quiescent state.

Cells are now ready to use for experiments.

FIGS. 9A-C present the appearance of macrophages on the surface of culture dishes and on cytodex beeds on day 38 ex vivo.

Example 4: Immortalization of Splenocytes with LIVeMac

When harvesting cells, first treat spleen with collagenase.

Separate cells by pushing spleen through a cell strainer and then separate PBMC using lymphocyte separation media.

After 1-2 days most cells will be dead (T, B, NK cells are in media without proper cytokines and most splenocytes fall in that category) but myeloid cells in the 1× GM-CSF media will be adherent. After approximately two days (after adherent myeloid cells appear, but before they die from exposure to dead cells), remove the supernatant, wash one time with PBS and then replace with new media.

The cells are kept in culture so that like the peripheral blood samples, they are harvested for transfection at day 4. Follow the protocol as above from here forward.

Example 5: Characterization of Immortalized Macrophages

Figure 11A:
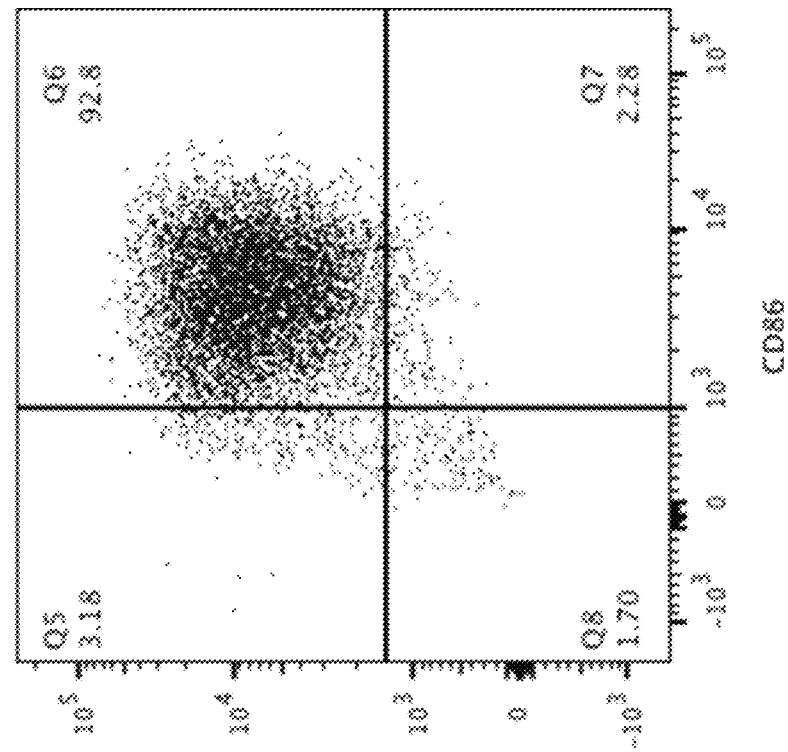
FIGS. 11A-B. Splenocyte cells immortalized with LIVeMac display positive staining for (FIG. 11A) CD11b and F4/80 and (FIG. 11B) CD80 and CD86, surface markers characteristic of mature macrophages, as determined by flow cytometry.
Figure 11B:
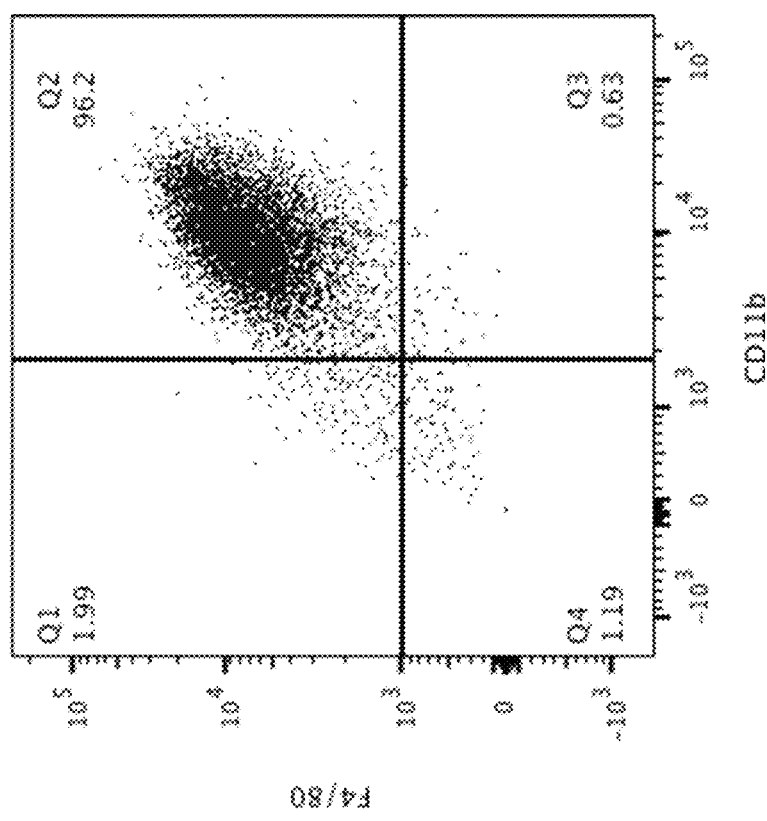
Figure 12:
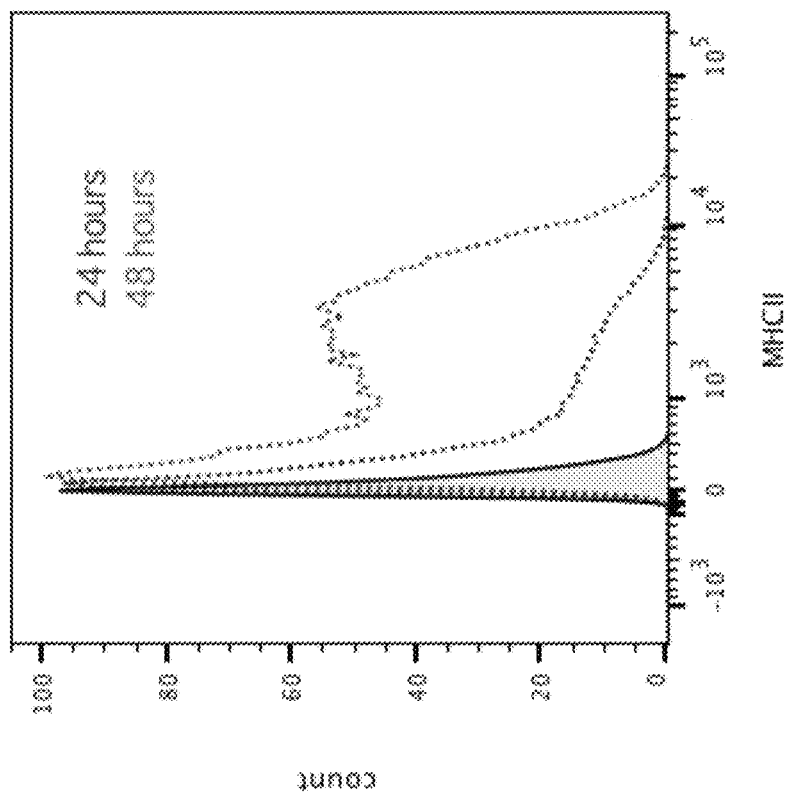
FIG. 12. Peripheral blood derived mononuclear cells immortalized with LIVeMac are IFNγ responsive. Macrophages were treated with 100 U/mL of rmIFNγ for 24 or 48 hours, and then stained for MHC II and analyzed by flow cytometry. By 48 hours, all cells had upregulated MHC II, indication that these macrophages are interferon-responsive.
Figure 13:
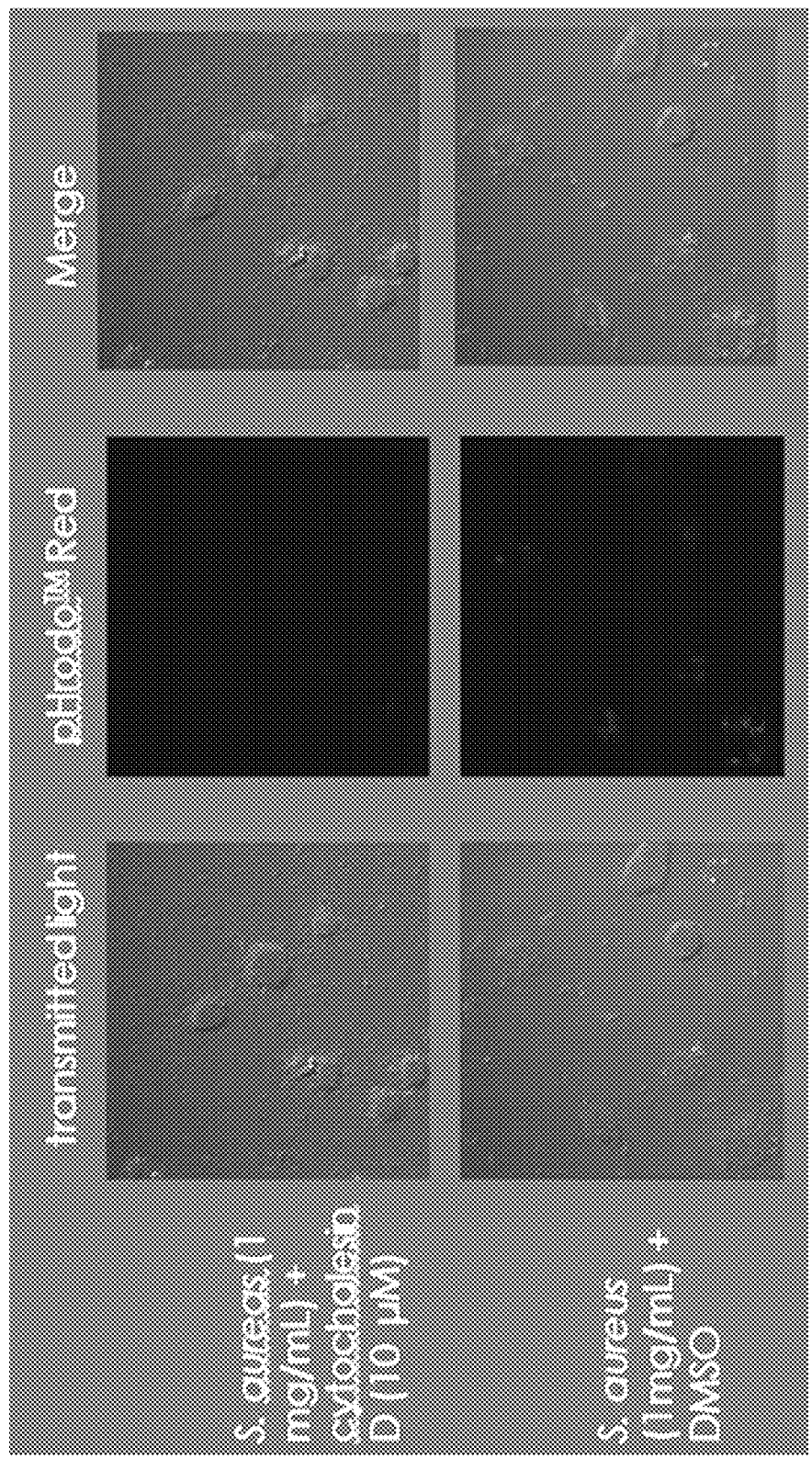
FIG. 13. Macrophages immortalized with LIVeMac are phagocytic. Confocal images of immortalized macrophage treated with DMSO or cytochalasin D and then infected with pHrodo Red *Staphylococcus aureus* Bioparticles® for 60 minutes. These bioparticles will only fluoresce when the pH of the environment is low. Thus, fluorescence can be detected when the bacteria reach the lysosome. Macrophages pretreated with cytochalasin D are unable to undergo phagocytosis while those mock treated with DMSO are able to phagocytose the *S. aureus* in their environment, as indicated by the internalized red fluorescent bacteria.
Figure 14:
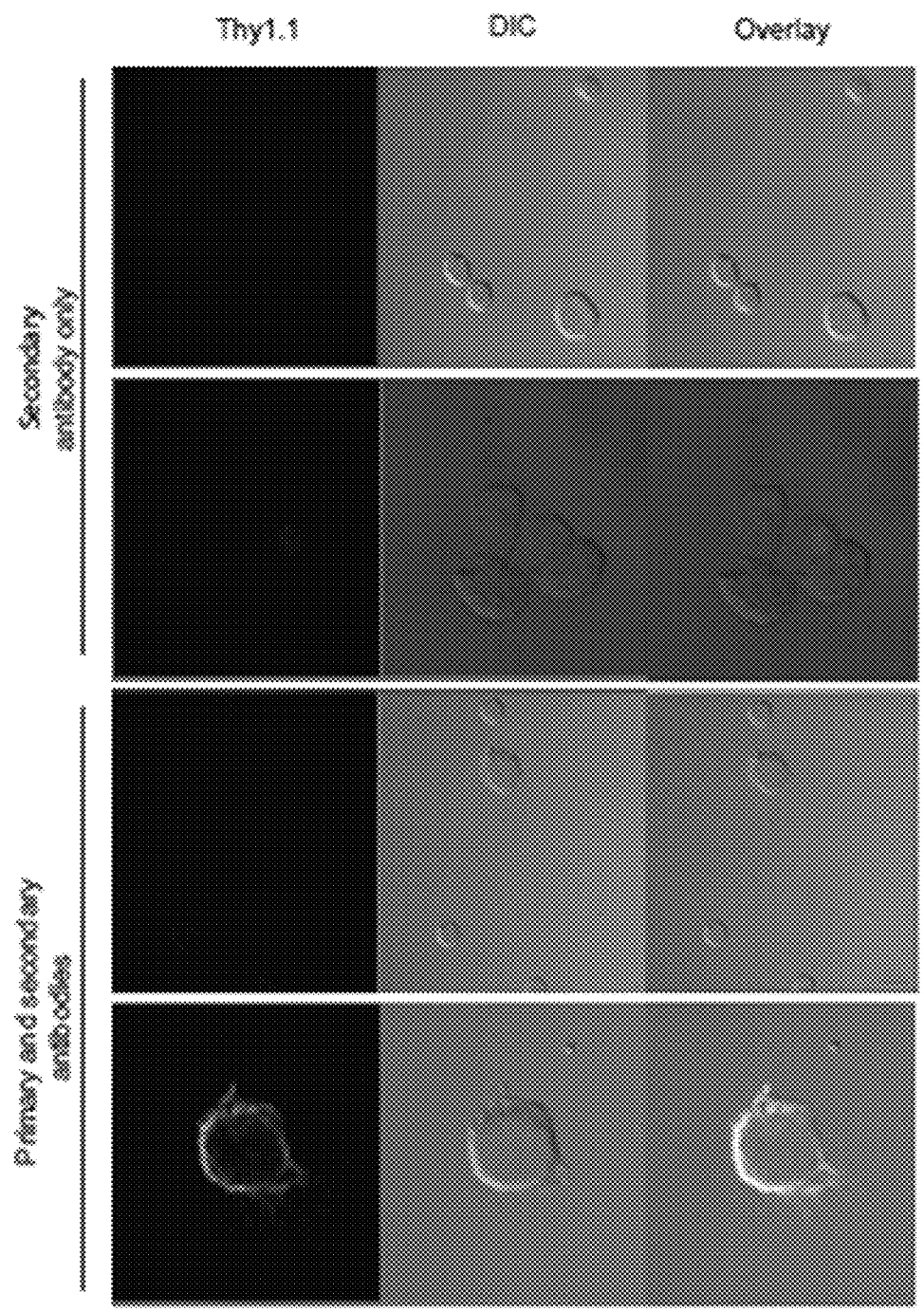
FIG. 14. Splenocytes cultured in 1× GM-CSF for four days were transduced with the multicistronic LIVeMac and maintained in 1× GM-CSF for an additional 10 days before being moved to growth factor free media. Cells were stained 21 days ex vivo with anti-Thy1.1-Biotin and anti-streptavidin AlexaFluor 647 or with streptavidin AlexaFluor 647 only.

Immortalized macrophage prepared by transducing mouse PBMCs with LIVeMac were stained for cell surface markers and analyzed by flow cytometry. Results presented in FIG. 10 indicate that the cells were mature macrophage because they are negative for cell surface markers of immature myeloid progenitor cells, c-kit, CD34, and Flt3 (FIGS. 10A-C) positive for CD11b (FIG. 10D) and F4-80 (FIG. 11). These cells are also negative for markers of granulocytes (FIGS. 10 E-G). The cells are also positive for CD64 and weakly positive for CD11c (FIGS. 10 H-I), consistent with a macrophage phenotype. Like primary macrophage, the immortalized macrophage responded to gamma-interferon by upregulating expression of MHC II as illustrated in FIG. 11. Additionally, the immortalized macrophages were competent for phagocytosis, as illustrated in FIG. 12. Splenocytes transduced with the multicistronic virus maintained a morphology consistent with macrophages and monocytes. Thy1.1 was detected on the surface of these transduced cells as illustrated in FIG. 13.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed:

1. A replication-deficient viral vector for immortalizing mammalian cells, wherein the replication-deficient viral vector comprises a polynucleotide encoding:
   the p30Gag-vRaf-T2A-vMyc fusion protein of SEQ ID NO: 1;
   the Thy1.1 protein of SEQ ID NO: 3 and the p30Gag-vRaf-T2A-vMyc fusion protein of SEQ ID NO: 1; or
   the Thy1.1-P2A-p30Gag-vRaf-T2A-vMyc fusion protein of SEQ ID NO: 2.

2. The replication-deficient viral vector of claim 1, wherein the replication-deficient viral vector comprises a polynucleotide encoding the p30Gag-vRaf-T2A-vMyc fusion protein of SEQ ID NO: 1 further comprises a polynucleotide encoding a surface marker.

3. The replication-deficient viral vector of claim 2, wherein the polynucleotide encoding a surface marker encodes a thy1.1 protein comprising a sequence having at least 95% identity to SEQ ID NO: 3.

4. The replication-deficient viral vector of claim 3, wherein the polynucleotide encoding the thy 1.1 protein comprising the sequence having at least 95% identity to SEQ ID NO: 3 is operatively linked to an internal ribosome entry site.

5. The replication-deficient viral vector of claim 1, wherein the vector is a lentiviral vector.

6. A host cell comprising the replication-deficient viral vector of claim 1.

7. The host cell of claim 6, wherein the cell is a HEK-293T cell.

8. A replication-deficient virus produced by the host cell of claim 6.

9. The replication-deficient viral vector of claim 1, wherein the polynucleotide encoding the thy1.1 protein is operatively linked to an internal ribosome entry site.

* * * * *